United States Patent
Rashid et al.

(10) Patent No.: US 11,851,488 B2
(45) Date of Patent: Dec. 26, 2023

(54) ANTI-CD3-FOLATE CONJUGATES AND THEIR USES

(71) Applicant: Ambrx, Inc., La Jolla, CA (US)

(72) Inventors: Harun Rashid, San Diego, CA (US);
Feng Tian, San Diego, CA (US);
Marco Gymnopoulos, San Diego, CA (US)

(73) Assignee: Ambrx, Inc., La Jolla, CA (US)

( * ) Notice: Subject to any disclaimer, the term of this patent is extended or adjusted under 35 U.S.C. 154(b) by 0 days.

(21) Appl. No.: 15/773,167

(22) PCT Filed: Nov. 2, 2016

(86) PCT No.: PCT/US2016/060087
§ 371 (c)(1),
(2) Date: May 3, 2018

(87) PCT Pub. No.: WO2017/079272
PCT Pub. Date: May 11, 2017

(65) Prior Publication Data
US 2018/0319885 A1    Nov. 8, 2018

Related U.S. Application Data

(60) Provisional application No. 62/374,693, filed on Aug. 12, 2016, provisional application No. 62/267,086, filed on Dec. 14, 2015, provisional application No. 62/250,451, filed on Nov. 3, 2015.

(51) Int. Cl.
| | |
|---|---|
| C07K 16/28 | (2006.01) |
| A61K 47/68 | (2017.01) |
| A61K 39/395 | (2006.01) |
| A61K 31/522 | (2006.01) |
| A61K 39/00 | (2006.01) |

(52) U.S. Cl.
CPC ........ *C07K 16/2809* (2013.01); *A61K 31/522* (2013.01); *A61K 39/395* (2013.01); *A61K 47/6803* (2017.08); *A61K 47/6849* (2017.08); *A61K 2039/505* (2013.01); *C07K 2317/55* (2013.01); *C07K 2317/622* (2013.01); *C07K 2317/92* (2013.01); *C07K 2317/94* (2013.01)

(58) Field of Classification Search
CPC .................................................. C07K 16/2809
USPC ....................................................... 424/136.1
See application file for complete search history.

(56) References Cited

U.S. PATENT DOCUMENTS

| | | |
|---|---|---|
| 3,773,919 A | 11/1973 | Boswell |
| 4,414,148 A | 11/1983 | Jansen |
| 4,485,045 A | 11/1984 | Regen |
| 4,542,225 A | 9/1985 | Blattler |
| 4,544,545 A | 10/1985 | Ryan |
| 4,569,789 A | 2/1986 | Blattler |
| 4,589,071 A | 5/1986 | Yamamuro |
| 4,618,492 A | 10/1986 | Blattler |
| 4,625,014 A | 11/1986 | Senter |
| 4,659,839 A | 4/1987 | Nicolotti |
| 4,671,958 A | 6/1987 | Rodwell |
| 4,680,338 A | 7/1987 | Sundoro |
| 4,699,784 A | 10/1987 | Shih |
| 4,904,584 A | 2/1990 | Shaw |
| 5,252,714 A | 10/1993 | Harris |
| 5,480,981 A | 1/1996 | Goodwin |
| 9,587,021 B2 * | 3/2017 | Huang ............... C07K 16/2803 |
| 2013/0274446 A1 | 10/2013 | Kumagai |
| 2014/0099318 A1 * | 4/2014 | Huang ............... C07K 16/2863 424/139.1 |
| 2014/0302064 A1 | 10/2014 | Moore |
| 2016/0194399 A1 * | 7/2016 | Irving ................ A61K 39/395 435/69.6 |
| 2017/0121420 A1 * | 5/2017 | Heidrich ........... C07K 16/3046 |
| 2017/0137519 A1 * | 5/2017 | Huang ............... C07K 16/2863 |
| 2021/0179734 A1 * | 6/2021 | Bailey ............... C07K 16/2809 |
| 2021/0317213 A1 * | 10/2021 | Rashid .............. A61K 47/6803 |
| 2022/0041721 A1 * | 2/2022 | Zhang ............... C07K 16/2851 |
| 2022/0226488 A1 * | 7/2022 | Moon ..................... A61P 35/00 |

FOREIGN PATENT DOCUMENTS

| | | |
|---|---|---|
| CN | 102618605 | 8/2012 |
| CN | 102618605 A | 8/2012 |
| CN | 102618605 A | 8/2012 |
| CN | 103703024 | 4/2014 |
| CN | 103703024 A | 4/2014 |
| CN | 103703024 A | 4/2014 |
| EP | 0 36 676 A1 | 9/1981 |
| EP | 36676 A1 | 9/1981 |
| EP | 0 143 949 A1 | 6/1985 |
| EP | 143949 A1 | 6/1985 |
| EP | 0 058 481 A1 | 8/1985 |
| EP | 58481 A1 | 8/1985 |
| EP | 0 188 256 A2 | 7/1986 |
| EP | 188256 A2 | 7/1986 |
| EP | 2 840 091 A1 | 2/2015 |

(Continued)

OTHER PUBLICATIONS

Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Kularatne et al. (Angew Chem Int Ed Engl. Nov. 11, 2013; 52(46): 12101-12104).*
Kim et al. (J Am Chem Soc. Jun. 20, 2012; 134(24): 9918-9921).*
Lim et al.(Critical Rev Biotechnology Oct. 2016;36(5):803-15; Epub Jun. 3, 2015).*
Kularatne et al. (Angew Chem Int Ed Engl. Nov. 11, 2013; 52(46): 12101-12104. doi:10.1002/anie.201306866).*
Ward et al., 1989, Nature 341, 554-546.

(Continued)

*Primary Examiner* — Lynn A Bristol
(74) *Attorney, Agent, or Firm* — Ambrx, Inc.

(57) ABSTRACT

Described herein are novel anti-CD3 antibodies conjugated to folate and uses thereof treatment of diseases or conditions that would benefit from such conjugate are provided.

23 Claims, 8 Drawing Sheets
Specification includes a Sequence Listing.

(56) References Cited

FOREIGN PATENT DOCUMENTS

| | | | |
|---|---|---|---|
| EP | 2840091 A1 | 2/2015 |
| JP | 2007-525943 | 9/2007 |
| JP | 2007-525943 A | 9/2007 |
| JP | 2007-525943 A | 9/2007 |
| JP | 2007-536899 | 12/2007 |
| JP | 2007-536899 A | 12/2007 |
| JP | 2007-536899 A | 12/2007 |
| JP | 2014/517844 | 7/2014 |
| JP | 2014-517844 A | 7/2014 |
| JP | 2014-517844 A | 7/2014 |
| WO | WO96/32478 A1 | 10/1996 |
| WO | WO 9632478 A1 | 10/1996 |
| WO | WO97/34631 A1 | 9/1997 |
| WO | WO 9734631 A1 | 9/1997 |
| WO | WO99/03887 A1 | 1/1999 |
| WO | WO 9903887 A1 | 1/1999 |
| WO | WO99/67291 A2 | 12/1999 |
| WO | WO 9967291 A2 | 12/1999 |
| WO | WO00/26354 A1 | 11/2000 |
| WO | WO 0026354 A1 | 11/2000 |
| WO | WO03/101972 A1 | 12/2003 |
| WO | WO 03101972 A1 | 12/2003 |
| WO | 2004/094593 A2 | 11/2004 |
| WO | WO2004/094593 A2 | 11/2004 |
| WO | 2005/003294 A2 | 1/2005 |
| WO | WO2005/003294 A2 | 1/2005 |
| WO | 2009/024771 A2 | 2/2009 |
| WO | WO 2009/024771 | * 2/2009 |
| WO | 2012/020622 A1 | 2/2012 |
| WO | WO 2012/020622 A1 | 2/2012 |
| WO | 2012/158818 A2 | 11/2012 |
| WO | 2012/162067 A2 | 11/2012 |
| WO | WO2012/158818 A2 | 11/2012 |
| WO | WO2012/162067 A2 | 11/2012 |
| WO | 2013/092001 A1 | 6/2013 |
| WO | WO2013/092001 A1 | 6/2013 |
| WO | 2015/006749 A2 | 1/2015 |
| WO | WO2015/006749 A2 | 1/2015 |
| WO | 2015/026894 A2 | 2/2015 |
| WO | WO2015/026894 A2 | 2/2015 |

OTHER PUBLICATIONS

Masat, L. et al., 1994, PNAS 91:893-896.
Hu, S-Z et al., 1996, Cancer Research, 56:3055-3061.
Pessi et al., 1993, Nature 362:367-369.
Martin, et al., 1994, EMBO J. 13:5303-5309.
Holliger, P. et al., 1003, PNAS 90:6444-6448.
Jones et al., 1986, Nature 321:522-525.
Riechmann et al., 1988 Nature 332:323-327.
McCafferty et al., 1990, Nature 348:552-554.
Clark, R. et al., 1996, J. Biol, Chem. 271:21969-21977.
Tornoe et al., 2002, Org. Chem. 67:3057-3064.
Rostovtsev et al., 2002, Angew. Chem, Int. Ed. 41:2596-2599.
Kabat et al., Sequences of Proteins of Immunological Interest, 5th Ed. Public Health Service, National Institutes of Health, Bethesda, MD. 1991.
Hawkins et al. J. Mol. Biol. , 1992, 226:889-896.
Barbas III et al., PNAS (USA) 1994, 91:3809-3813.
Yang et al., J. Mol. Biol, 1995, 254:392403.
Schier et al., J. Mol, Biol., 1996, 263:551-567.
Thompson et al., J. Mol. Biol, 1996, 256:77-88.
Balint and Larrick, Gene, 1993, 137:109-118.
Wu et al. PNAS (USA), 1998, 95:6037-6042.
Chiswell and McCafferty, TIBTECH, 1992, 10:80-84.
Rader and Barbas III, 1997, Current Opinion in Biotech, 8:503-508.
Maynard and Georgiou, 2000, Annu. Rev. Biomed. Eng. 2:339-76.
Hudson, 1998, Curr Opin. Biotechnol. 9:395-402.
Bruggemann and Taussig, 1997, Curr. Opin. Biotechnol. 8:455-458.
Griffiths and Duncan, 1998, Curr. Opin. Biotechnol. 9:102-108.
Clark, 2000, Immunol. Today, 21:397-402.
Leong, S.R. et al., 2001, Cytokine, 16:106-119.
Batzer et al., 1991, Nucleic Acid Res., 19:5081.
Ohtsuka et al., 1985, J. Biol. Chem., 260:2695-2608.
Rossolini et al., 1994, Mol. Cell Probes 8:91-98.
Creighton, Dec. 1993, Proteins: Structures and Molecular Properties (W H Freeman & Co.: 2nd edition).
Rader et al., 2003, Proc. Natl. Acad. Sci. USA, Apr. 29; 100(9):5396-400.
Padwa, A., 1991, Comprehensive Organic Synthesis, vol. 4, Ed. Trost, B.M. , Pergamon, Oxford, p. 1069-1109.
Huisgen, R. 1.3-Dipolar Cycloaddition Chemistry, 1984, Ed. Padwa, A., Wiley, New York, p. 1-176.
Capon, et al., 1989, Nature, 337:525-331.
Zheng, X. et al., 1995, The Journal of Immunology, 154:5590-5600.
Fisher, C. et al., 1996, N. Engl. J. Med, 334:1697-1702.
Van Zee K. et al., 1996, The Journal of Immunology, 156: 2221-2230.
Moreland et al., 1997, N. Engl. J. Med., 337:141-147.
Harvill et al., 1995, Immuunotechnology, 1:95-105.
Sidman et al., 1983, Biopolymers, 22:547-556.
Eppstein et al., 1985, Proc. Natl Acad. Sci. USA, 82:3688-3692.
Hwang et al., 1980, Proc. Natl. Acad. Sci. USA, 77:4030-4034.
Park JW et al., 1995, Proc. Natl. Acad. Sci. USA, 92:1327-1331.
Lasic D and Papahadjopoulos D (eds): Medical Applications of Liposomes, 1998.
Park JW et al., 2002, Clin. Cancer Res., 8:1172-1181.
Neilsen UB et al., 2002, Biochim. Biophys. Acta, 1591 (1-3):109-118.
Mamot C et al., 2003, Cancer Res., 63:3154-3161.
Boissel et al., 1993, 268:15983-93.
Masat, L. et al., 1994, Proc. Natl. Acad. Sci. USA 91:893-896.
Holliger P. et al., 1993, Proc. Natl. Acad. Sci. USA 90:6444-6448.
Park J.W. et al., Clin. Cancer Res., 2002, 8:1172-1181.
Barbas C.F. et al., Proc. Natl. Acad. Sci. USA 1994, 91:3809-3813.
Wu et al. Proc. Natl. Acad. Sci. USA, 1998, 95:6037-6042.
Rader and Barbas, Current Opinion in Biotech, 1997, 8:503-508.
Maynard and Georgiou, Annu. Rev. Biomed. Eng., 2000, 2:339-76.
Hudson, Curr Opin. Biotechnol., 1998, 9:395-402.
Bruggemann and Taussig, Curr. Opin. Biotechnol., 1997, 8:455-458.
Griffiths and Duncan, Curr. Opin. Biotechnol., 1998, 9:102-108.
Clark, Immunol. Today, 2000, 21:397-402.
Leong, S.R. et al., Cytokine, 2001, 16:106-119.
Batzer et al., Nucleic Acid Res., 1991,19:5081.
Ohtsuka et al., J. Biol. Chem., 1985, 260:2605-2608.
Rossolini et al., Mol. Cell Probes, 1994, 8:91-98.
Park, JW et al., Proc. Natl. Acad. Sci. USA, 1995, 92:1327-1331.
Rader et al., Proc. Natl. Acad. Sci. USA, Apr. 29; 2003, 100(9):5396-400.
Padwa, A., Comprehensive Organic Synthesis, vol. 4, Ed. Trost, B.M., Pergamon, Oxford, 1991, p. 1069-1109.
Huisgen, R. 1,3-Dipolar Cycloaddition Chemistry, Ed. Padwa, A., Wiley, New York, 1984, p. 1-176.
Capon et al., Nature, 1989, 337:525-331.
Zheng, X. et al., J. Immunol. 1995, 154:5590-5600.
Fisher, C. et al., N. Engl. J. Med., 1996, 334:1697-1702.
Van Zee K. et al., J. Immunol. 1996, 156: 2221-2230.
Moreland et al., N. Engl. J. Med., 1997, 337:141-147.
Harvill et al., Immunotechnology, 1995 1:95-105.
Sidman et al., Biopolymers, 1983, 22:547-556.
Eppstein et al., Proc. Natl Acad. Sci. USA, 1985, 82:3688-3692.
Hwang et al., Proc. Natl. Acad. Sci. USA, 1980, 77:4030-4034.
Kularatne S. A. et al., Angewandte Chemie (International Edition), vol. 52, No. 46, 11, pp. 12101-12104, 2013.
Kranz D. M. et al., PNAS US, vol. 92, pp. 9057-9061, 1995.
Zhao W. et al., Polymer, vol. 66, A1-A10, 2015.
Kularatne S. A. et al.,"Supporting Information—Recruiting Cytotoxic T Cells to Folate-Receptor-Positive Cancer Cells" Angewandte Chemie (International Edition), p. 1-12, Sep. 25, 2013 (supplementary information for Ref. #1).
Smith-Gill S. J. et al., J. Immunol. 139, pp. 4135-4144, 1987.
Kumar S. et al., J. Biol. Chem. 275, pp. 35129-35136, 2000.

(56) References Cited

OTHER PUBLICATIONS

Song M-K. et al., Biochem Biophys Res Comm., 268, pp. 390-394, 2000.
Kim C. H. et al., J Am Chem Soc., 134(24), pp. 9918-9992, 2012.
Lim S. I. and Kwon I, Critical Rev Biotechnology, 36(5), pp. 803-815, 2016.
Clakson T. and Wells J. A., Trends Biotechnol., 12, pp. 173-184, 1994.
Drummond D. C. et al., Liposomal drug delivery systems for cancer therapy, in Teicher B (ed): Cancer Drug Discovery and Development, 2002.
Langer R., Chem. Tech., 12, pp. 98-105, 1982.
Lowman H. B. et al., Biochemistry, 30, pp. 10832-10838, 1991.
Smyth M. L. and Von Itzstein M., J. Am. Chem. Soc, 116, pp 2725-2733, 1994.
Winter G. et al., Annu. Rev. Immunol., 12, pp 433-455, 1994.
Venturini S. et al., Protein Peptide Letters, pp. 70-75, 1994.
O'Neil K.T. et al., Techniques in Protein Chemistry V (Crabb, L., ed.), pp 517-524, Academic Press, San Diego, 1994.
McConnell S. J. and HOESS R. H., J. Mol. Biol., 250, pp. 4460-4470, 1995.
Langer R. et al., J. Biomed. Mater. Res., 15, pp. 167-277, 1981.

\* cited by examiner

A.

B.

SEQUENCE LISTING

```
<160> NUMBER OF SEQ ID NOS: 15

<210> SEQ ID NO 1
<211> LENGTH: 125
<212> TYPE: PRT
<213> ORGANISM: Artificial Sequence
<220> FEATURE:
<223> OTHER INFORMATION: Humanized variable heavy chain sequence of
      anti-CD3 antibody

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
```

```
                    50                  55                  60

Ser Val Lys Asp Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                     85                  90                  95

Tyr Cys Val Arg His Gly Asn Phe Gly Asn Ser Tyr Val Ser Trp Phe
                    100                 105                 110

Ala Tyr Trp Gly Gln Gly Thr Leu Val Thr Val Ser Ser
                    115                 120                 125

<210> SEQ ID NO 2
<211> LENGTH: 125
<212> TYPE: PRT
<213> ORGANISM: Artificial Sequence
<220> FEATURE:
<223> OTHER INFORMATION: Humanized variable heavy chain sequence of
      anti-CD3 antibody

<400> SEQUENCE: 2

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Thr Tyr
                 20                  25                  30

Ala Met Asn Trp Val Arg Gln Ala Pro Gly Lys Gly Leu Glu Trp Val
             35                  40                  45

Ala Arg Ile Arg Ser Lys Tyr Asn Asn Tyr Ala Thr Tyr Tyr Ala Asp
         50                  55                  60

Ser Val Lys Asp Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                     85                  90                  95

Tyr Cys Val Arg His Gly Asn Phe Gly Asn Ser Tyr Val Ser Trp Phe
                    100                 105                 110

Ala Tyr Trp Gly Gln Gly Thr Leu Val Thr Val Ser Ser
                    115                 120                 125

<210> SEQ ID NO 3
<211> LENGTH: 125
<212> TYPE: PRT
<213> ORGANISM: Artificial Sequence
<220> FEATURE:
<223> OTHER INFORMATION: Humanized variable heavy chain sequence of
      anti-CD3 antibody

<400> SEQUENCE: 3

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Thr Tyr
                 20                  25                  30

Ala Met Asn Trp Val Arg Gln Ala Pro Gly Lys Gly Leu Glu Trp Val
             35                  40                  45

Ala Arg Ile Arg Ser Lys Tyr Asn Asn Tyr Ala Thr Tyr Tyr Ala Asp
         50                  55                  60

Ser Val Lys Asp Arg Phe Thr Ile Ser Arg Asp Asp Ser Lys Asn Ile
 65                  70                  75                  80

Leu Tyr Leu Gln Met Asn Ser Leu Lys Thr Glu Asp Thr Ala Val Tyr
                     85                  90                  95

Tyr Cys Val Arg His Gly Asn Phe Gly Asn Ser Tyr Val Ser Trp Phe
```

```
                      100                 105                 110
Ala Tyr Trp Gly Gln Gly Thr Leu Val Thr Val Ser Ser
            115                 120                 125

<210> SEQ ID NO 4
<211> LENGTH: 110
<212> TYPE: PRT
<213> ORGANISM: Artificial Sequence
<220> FEATURE:
<223> OTHER INFORMATION: Humanized variable light chain sequence of
      anti-CD3 antibody

<400> SEQUENCE: 4

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Thr
        35                  40                  45

Leu Ile Tyr Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly
            100                 105                 110

<210> SEQ ID NO 5
<211> LENGTH: 110
<212> TYPE: PRT
<213> ORGANISM: Artificial Sequence
<220> FEATURE:
<223> OTHER INFORMATION: Humanized variable light chain sequence of
      anti-CD3 antibody

<400> SEQUENCE: 5

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly
            100                 105                 110

<210> SEQ ID NO 6
<211> LENGTH: 110
<212> TYPE: PRT
<213> ORGANISM: Artificial Sequence
<220> FEATURE:
<223> OTHER INFORMATION: Humanized variable light chain sequence of
      anti-CD3 antibody

<400> SEQUENCE: 6
```

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
50                  55                  60

Ser Gly Ser Leu Leu Gly Gly Lys Ala Ala Leu Thr Leu Ser Gly Ala
65              70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly
            100                 105                 110
```

<210> SEQ ID NO 7
<211> LENGTH: 235
<212> TYPE: PRT
<213> ORGANISM: Artificial Sequence
<220> FEATURE:
<223> OTHER INFORMATION: Humanized variable heavy and light chain sequence of anti-CD3 antibody

<400> SEQUENCE: 7

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
50                  55                  60

Ser Val Lys Asp Arg Phe Thr Ile Ser Arg Asp Asp Ser Lys Asn Ser
65              70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Gln Ala Val
            115                 120                 125

Val Thr Gln Glu Pro Ser Leu Thr Val Ser Pro Gly Gly Thr Val Thr
130                 135                 140

Leu Thr Cys Arg Ser Ser Thr Gly Ala Val Thr Thr Ser Asn Tyr Ala
145                 150                 155                 160

Asn Trp Phe Gln Gln Lys Pro Gly Gln Ala Pro Arg Thr Leu Ile Tyr
                165                 170                 175

Gly Thr Asn Lys Arg Ala Pro Trp Thr Pro Ala Arg Phe Ser Gly Ser
            180                 185                 190

Leu Leu Gly Gly Lys Ala Ala Leu Thr Leu Ser Gly Ala Gln Pro Glu
        195                 200                 205

Asp Glu Ala Glu Tyr Tyr Cys Ala Leu Trp Tyr Ser Asn Leu Trp Val
    210                 215                 220

Phe Gly Gly Gly Thr Lys Leu Thr Val Leu Gly
225                 230                 235
```

```
<210> SEQ ID NO 8
<211> LENGTH: 235
<212> TYPE: PRT
<213> ORGANISM: Artificial Sequence
<220> FEATURE:
<223> OTHER INFORMATION: Humanized variable heavy and light chain
      sequence of anti-CD3 antibody

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Gln Ala Val
        115                 120                 125

Val Thr Gln Glu Pro Ser Leu Thr Val Ser Pro Gly Gly Thr Val Thr
    130                 135                 140

Leu Thr Cys Arg Ser Ser Thr Gly Ala Val Thr Thr Ser Asn Tyr Ala
145                 150                 155                 160

Asn Trp Val Gln Gln Lys Pro Gly Gln Ala Pro Arg Gly Leu Ile Gly
                165                 170                 175

Gly Thr Asn Lys Arg Ala Pro Gly Val Pro Ala Arg Phe Ser Gly Ser
            180                 185                 190

Leu Leu Gly Gly Lys Ala Ala Leu Thr Leu Ser Gly Ala Gln Pro Glu
        195                 200                 205

Asp Glu Ala Glu Tyr Tyr Cys Ala Leu Trp Tyr Ser Asn Leu Trp Val
    210                 215                 220

Phe Gly Gly Gly Thr Lys Leu Thr Val Leu Gly
225                 230                 235

<210> SEQ ID NO 9
<211> LENGTH: 235
<212> TYPE: PRT
<213> ORGANISM: Artificial Sequence
<220> FEATURE:
<223> OTHER INFORMATION: Humanized variable heavy and light chain
      sequence of anti-CD3 antibody

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
```

```
                65                  70                  75                  80
Leu Tyr Leu Gln Met Asn Ser Leu Lys Thr Glu Asp Thr Ala Val Tyr
                    85                  90                  95

Tyr Cys Val Arg His Gly Asn Phe Gly Asn Ser Tyr Val Ser Trp Phe
                    100                 105                 110

Ala Tyr Trp Gly Gln Gly Thr Leu Val Thr Val Ser Gln Ala Val
                    115                 120                 125

Val Thr Gln Glu Pro Ser Leu Thr Val Ser Pro Gly Gly Thr Val Thr
        130                 135                 140

Leu Thr Cys Arg Ser Ser Thr Gly Ala Val Thr Thr Ser Asn Tyr Ala
145                 150                 155                 160

Asn Trp Val Gln Gln Lys Pro Gly Gln Ala Pro Arg Gly Leu Ile Gly
                    165                 170                 175

Gly Thr Asn Lys Arg Ala Pro Gly Thr Pro Ala Arg Phe Ser Gly Ser
                    180                 185                 190

Leu Leu Gly Gly Lys Ala Ala Leu Thr Leu Ser Gly Ala Gln Pro Glu
                    195                 200                 205

Asp Glu Ala Glu Tyr Tyr Cys Ala Leu Trp Tyr Ser Asn Leu Trp Val
        210                 215                 220

Phe Gly Gly Gly Thr Lys Leu Thr Val Leu Gly
225                 230                 235

<210> SEQ ID NO 10
<211> LENGTH: 235
<212> TYPE: PRT
<213> ORGANISM: Artificial Sequence
<220> FEATURE:
<223> OTHER INFORMATION: Humanized variable heavy and light chain
      sequence of anti-CD3 antibody

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                    85                  90                  95

Tyr Cys Val Arg His Gly Asn Phe Gly Asn Ser Tyr Val Ser Trp Phe
                    100                 105                 110

Ala Tyr Trp Gly Gln Gly Thr Leu Val Thr Val Ser Gln Ala Val
                    115                 120                 125

Val Thr Gln Glu Pro Ser Leu Thr Val Ser Pro Gly Gly Thr Val Thr
        130                 135                 140

Leu Thr Cys Arg Ser Ser Thr Gly Ala Val Thr Thr Ser Asn Tyr Ala
145                 150                 155                 160

Asn Trp Phe Gln Gln Lys Pro Gly Gln Ala Pro Arg Thr Leu Ile Tyr
                    165                 170                 175

Gly Thr Asn Lys Arg Ala Pro Trp Thr Pro Ala Arg Phe Ser Gly Ser
                    180                 185                 190
```

```
Leu Leu Gly Gly Lys Ala Ala Leu Thr Leu Ser Gly Ala Gln Pro Glu
            195                 200                 205

Asp Glu Ala Glu Tyr Tyr Cys Ala Leu Trp Tyr Ser Asn Leu Trp Val
        210                 215                 220

Phe Gly Gly Gly Thr Lys Leu Thr Val Leu Gly
225                 230                 235

<210> SEQ ID NO 11
<211> LENGTH: 235
<212> TYPE: PRT
<213> ORGANISM: Artificial Sequence
<220> FEATURE:
<223> OTHER INFORMATION: Humanized variable heavy and light chain
      sequence of anti-CD3 antibody

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Gln Ala Val
        115                 120                 125

Val Thr Gln Glu Pro Ser Leu Thr Val Ser Pro Gly Gly Thr Val Thr
    130                 135                 140

Leu Thr Cys Arg Ser Ser Thr Gly Ala Val Thr Thr Ser Asn Tyr Ala
145                 150                 155                 160

Asn Trp Val Gln Gln Lys Pro Gly Gln Ala Pro Arg Gly Leu Ile Gly
                165                 170                 175

Gly Thr Asn Lys Arg Ala Pro Gly Val Pro Ala Arg Phe Ser Gly Ser
            180                 185                 190

Leu Leu Gly Gly Lys Ala Ala Leu Thr Leu Ser Gly Ala Gln Pro Glu
        195                 200                 205

Asp Glu Ala Glu Tyr Tyr Cys Ala Leu Trp Tyr Ser Asn Leu Trp Val
    210                 215                 220

Phe Gly Gly Gly Thr Lys Leu Thr Val Leu Gly
225                 230                 235

<210> SEQ ID NO 12
<211> LENGTH: 235
<212> TYPE: PRT
<213> ORGANISM: Artificial Sequence
<220> FEATURE:
<223> OTHER INFORMATION: Humanized variable heavy and light chain
      sequence of anti-CD3 antibody

<400> SEQUENCE: 12

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Gln Ala Val
        115                 120                 125

Val Thr Gln Glu Pro Ser Leu Thr Val Ser Pro Gly Gly Thr Val Thr
    130                 135                 140

Leu Thr Cys Arg Ser Ser Thr Gly Ala Val Thr Thr Ser Asn Tyr Ala
145                 150                 155                 160

Asn Trp Val Gln Gln Lys Pro Gly Gln Ala Pro Arg Gly Leu Ile Gly
                165                 170                 175

Gly Thr Asn Lys Arg Ala Pro Gly Thr Pro Ala Arg Phe Ser Gly Ser
            180                 185                 190

Leu Leu Gly Gly Lys Ala Ala Leu Thr Leu Ser Gly Ala Gln Pro Glu
        195                 200                 205

Asp Glu Ala Glu Tyr Tyr Cys Ala Leu Trp Tyr Ser Asn Leu Trp Val
    210                 215                 220

Phe Gly Gly Gly Thr Lys Leu Thr Val Leu Gly
225                 230                 235

<210> SEQ ID NO 13
<211> LENGTH: 235
<212> TYPE: PRT
<213> ORGANISM: Artificial Sequence
<220> FEATURE:
<223> OTHER INFORMATION: Humanized variable heavy and light chain
      sequence of anti-CD3 antibody

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Gln Ala Val
        115                 120                 125

Val Thr Gln Glu Pro Ser Leu Thr Val Ser Pro Gly Gly Thr Val Thr
    130                 135                 140
```

```
Leu Thr Cys Arg Ser Ser Thr Gly Ala Val Thr Thr Ser Asn Tyr Ala
145                 150                 155                 160

Asn Trp Phe Gln Gln Lys Pro Gly Gln Ala Pro Arg Thr Leu Ile Tyr
            165                 170                 175

Gly Thr Asn Lys Arg Ala Pro Trp Thr Pro Ala Arg Phe Ser Gly Ser
        180                 185                 190

Leu Leu Gly Gly Lys Ala Ala Leu Thr Leu Ser Gly Ala Gln Pro Glu
            195                 200                 205

Asp Glu Ala Glu Tyr Tyr Cys Ala Leu Trp Tyr Ser Asn Leu Trp Val
        210                 215                 220

Phe Gly Gly Gly Thr Lys Leu Thr Val Leu Gly
225                 230                 235

<210> SEQ ID NO 14
<211> LENGTH: 235
<212> TYPE: PRT
<213> ORGANISM: Artificial Sequence
<220> FEATURE:
<223> OTHER INFORMATION: Humanized variable heavy and light chain
      sequence of anti-CD3 antibody

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Gln Ala Val
        115                 120                 125

Val Thr Gln Glu Pro Ser Leu Thr Val Ser Pro Gly Gly Thr Val Thr
    130                 135                 140

Leu Thr Cys Arg Ser Ser Thr Gly Ala Val Thr Thr Ser Asn Tyr Ala
145                 150                 155                 160

Asn Trp Val Gln Gln Lys Pro Gly Gln Ala Pro Arg Gly Leu Ile Gly
            165                 170                 175

Gly Thr Asn Lys Arg Ala Pro Gly Val Pro Ala Arg Phe Ser Gly Ser
        180                 185                 190

Leu Leu Gly Gly Lys Ala Ala Leu Thr Leu Ser Gly Ala Gln Pro Glu
            195                 200                 205

Asp Glu Ala Glu Tyr Tyr Cys Ala Leu Trp Tyr Ser Asn Leu Trp Val
        210                 215                 220

Phe Gly Gly Gly Thr Lys Leu Thr Val Leu Gly
225                 230                 235

<210> SEQ ID NO 15
<211> LENGTH: 235
<212> TYPE: PRT
```

<213> ORGANISM: Artificial Sequence
<220> FEATURE:
<223> OTHER INFORMATION: Humanized variable heavy and light chain
      sequence of anti-CD3 antibody

<400> SEQUENCE: 15

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Gln Ala Val
            115                 120                 125

Val Thr Gln Glu Pro Ser Leu Thr Val Ser Pro Gly Gly Thr Val Thr
    130                 135                 140

Leu Thr Cys Arg Ser Ser Thr Gly Ala Val Thr Thr Ser Asn Tyr Ala
145                 150                 155                 160

Asn Trp Val Gln Gln Lys Pro Gly Gln Ala Pro Arg Gly Leu Ile Gly
                165                 170                 175

Gly Thr Asn Lys Arg Ala Pro Gly Thr Pro Ala Arg Phe Ser Gly Ser
            180                 185                 190

Leu Leu Gly Gly Lys Ala Ala Leu Thr Leu Ser Gly Ala Gln Pro Glu
            195                 200                 205

Asp Glu Ala Glu Tyr Tyr Cys Ala Leu Trp Tyr Ser Asn Leu Trp Val
    210                 215                 220

Phe Gly Gly Gly Thr Lys Leu Thr Val Leu Gly
225                 230                 235
```

ANTI-CD3-FOLATE CONJUGATES AND THEIR USES

CROSS-REFERENCE TO RELATED APPLICATIONS

This application is a U.S. National Stage entry under 35 U.S.C § 371 of International Application No, PCT/US2016/060087, filed on Nov. 2, 2016, which is incorporated by reference herein in its entirety and claims priority to and the benefit of U.S. Provisional Application Ser. No. 62/250,451 filed on Nov. 3, 2015, U.S. Provisional Application Ser. No. 62/267,086 filed on Dec. 14, 2015, and U.S. Provisional Application Ser. No. 62/374,693 filed on Aug. 12, 2016, the specification and contents of each of which is incorporated by reference herein in its entirety for all purposes.

FIELD OF THE INVENTION

This invention relates to anti-CD3 antibodies and fragments thereof conjugated to folate.

BACKGROUND OF THE INVENTION

A naturally produced antibody (Ab) is a tetrameric structure consisting of two identical immunoglobulin (Ig) heavy chains and two identical light chains. The heavy and light chains of an Ab consist of different domains. Each light chain has one variable domain (VL) and one constant domain (CL), while each heavy chain has one variable domain (VH) and three or four constant domains (CH). Each domain, consisting of about 110 amino acid residues, is folded into a characteristic β-sandwich structure formed from two β-sheets packed against each other, the immunoglobulin fold. The VL domains each have three complementarity determining regions (CDR1-3) and the VH domains each have up to four complimentarity determining regions (CDR1-4), that are loops, or turns, connecting β-strands at one end of the domains. The variable regions of both the light and heavy chains generally contribute to antigen specificity, although the contribution of the individual chains to specificity is not necessarily equal. Antibody molecules have evolved to bind to a large number of molecules by using randomized CDR loops.

Functional substructures of Abs can be prepared by proteolysis and by recombinant methods. They include the Fab fragment, which comprises the VH-CH1 domains of the heavy chain and the VL-CL1 domains of the light chain joined by a single interchain disulfide bond, and the Fv fragment, which comprises only the VH and VL domains, and the Fc portion which comprises the non-antigen binding region of the molecule. In some cases, a single VH domain retains significant affinity for antigen (Ward et al., 1989, Nature 341, 554-546). It has also been shown that a certain monomeric κ light chain will specifically bind to its antigen. (L. Masat et al., 1994, PNAS 91:893-896). Separated light or heavy chains have sometimes been found to retain some antigen-binding activity as well (Ward et al., 1989, Nature 341, 554-546).

Another functional substructure is a single chain Fv (scFv), comprised of the variable regions of the immunoglobulin heavy and light chain, covalently connected by a peptide linker (S-z Hu et al., 1996, Cancer Research, 56, 3055-3061). These small (Mr 25,000) proteins generally retain specificity and affinity for antigen in a single polypeptide and can provide a convenient building block for larger, antigen-specific molecules. The short half-life of scFvs in the circulation limits their therapeutic utility in many cases.

A small protein scaffold called a "minibody" was designed using a part of the Ig VH domain as the template (Pessi et al., 1993, Nature 362, 367-369). Minibodies with high affinity (dissociation constant ($K_d$) about $10^{-7}$ M) to interleukin-6 were identified by randomizing loops corresponding to CDR1 and CDR2 of VH and then selecting mutants using the phage display method (Martin et al., 1994, EMBO J. 13, 53035309).

Camels often lack variable light chain domains when IgG-like material from their serum is analyzed, suggesting that sufficient antibody specificity and affinity can be derived from VH domains (three or four CDR loops) alone. "Camelized" VH domains with high affinity have been made, and high specificity can be generated by randomizing only the CDR3.

An alternative to the "minibody" is the "diabody." Diabodies are small bivalent and bispecific antibody fragments, having two antigen-binding sites. The fragments comprise a heavy-chain variable domain ($V_H$) connected to a light-chain variable domain ($V_L$) on the same polypeptide chain ($V_H$-$V_L$). Diabodies are similar in size to the Fab fragment. By using a linker that is too short to allow pairing between the two domains on the same chain, the domains are forced to pair with the complementary domains of another chain and create two antigen-binding sites. These dimeric antibody fragments, or "diabodies," are bivalent and bispecific. See, P. Holliger et al., PNAS 90:6444-6448 (1993).

CDR peptides and organic CDR mimetics have been made (Dougall et al., 1994, Trends Biotechnol. 12, 372-379). CDR peptides are short, typically cyclic, peptides which correspond to the amino acid sequences of CDR loops of antibodies. CDR loops are responsible for antibody-antigen interactions. CDR peptides and organic CDR mimetics have been shown to retain some binding affinity (Smyth & von Itzstein, 1994, J. Am. Chem. Soc. 116, 2725-2733). Mouse CDRs have been grafted onto the human Ig framework without the loss of affinity (Jones et al., 1986, Nature 321, 522-525; Riechmann et al., 1988).

In the body, specific Abs are selected and amplified from a large library (affinity maturation). The processes can be reproduced in vitro using combinatorial library technologies. The successful display of Ab fragments on the surface of bacteriophage has made it possible to generate and screen a vast number of CDR mutations (McCafferty et al., 1990, Nature 348, 552-554; Barbas et al., 1991, Proc. Natl. Acad. Sci. USA 88,7978-7982; Winter et al., 1994, Annu. Rev. Immunol. 12, 433-455). An increasing number of Fabs and Fvs (and their derivatives) are produced by this technique. The combinatorial technique can be combined with Ab mimics.

A number of protein domains that could potentially serve as protein scaffolds have been expressed as fusions with phage capsid proteins. Review in Clackson & Wells, Trends Biotechnol. 12:173-184 (1994). Several of these protein domains have already been used as scaffolds for displaying random peptide sequences, including bovine pancreatic trypsin inhibitor (Roberts et al., PNAS 89:2429-2433 (1992)), human growth hormone (Lowman et al., Biochemistry 30:10832-10838 (1991)), Venturini et al., Protein Peptide Letters 1:70-75 (1994)), and the IgG binding domain of Streptococcus (O'Neil et al., Techniques in Protein Chemistry V (Crabb, L,. ed.) pp. 517-524, Academic Press, San Diego (1994)). These scaffolds have displayed a single randomized loop or region. Tendamistat has been used as a presentation scaffold on the filamentous phage M13 (McConnell and Hoess, 1995, J. Mal. Biol. 250:460-470).

Covalent attachment of the hydrophilic polymer poly (ethylene glycol), abbreviated PEG, is a method of increasing water solubility, bioavailability, increasing serum half-life, increasing therapeutic half-life, modulating immunogenicity, modulating biological activity, or extending the circulation time of many biologically active molecules, including proteins, peptides, and particularly hydrophobic molecules. PEG has been used extensively in pharmaceuticals, on artificial implants, and in other applications where biocompatibility, lack of toxicity, and lack of immunogenicity are of importance. In order to maximize the desired properties of PEG, the total molecular weight and hydration state of the PEG polymer or polymers attached to the biologically active molecule must be sufficiently high to impart the advantageous characteristics typically associated with PEG polymer attachment, such as increased water solubility and circulating half life, while not adversely impacting the bioactivity of the parent molecule.

PEG derivatives are frequently linked to biologically active molecules through reactive chemical functionalities, such as lysine, cysteine and histidine residues, the N-terminus and carbohydrate moieties. Proteins and other molecules often have a limited number of reactive sites available for polymer attachment. Often, the sites most suitable for modification via polymer attachment play a significant role in receptor binding, and are necessary for retention of the biological activity of the molecule. As a result, indiscriminate attachment of polymer chains to such reactive sites on a biologically active molecule often leads to a significant reduction or even total loss of biological activity of the polymer-modified molecule. R. Clark et al., (1996), J. Biol. Chem., 271:21969-21977. To form conjugates having sufficient polymer molecular weight for imparting the desired advantages to a target molecule, prior art approaches have typically involved random attachment of numerous polymer arms to the molecule, thereby increasing the risk of a reduction or even total loss in bioactivity of the parent molecule.

The ability to incorporate non-genetically encoded amino acids into proteins permits the introduction of chemical functional groups that could provide valuable alternatives to the naturally-occurring functional groups, such as the epsilon-$NH_2$ of lysine, the sulthydryl-SH of cysteine, the imino group of histidine, etc. Certain chemical functional groups are known to be inert to the functional groups found in the 20 common, genetically-encoded amino acids but react cleanly and efficiently to form stable linkages. Azide and acetylene groups, for example, are known in the art to undergo a Huisgen [3+2] cycloaddition reaction in aqueous conditions in the presence of a catalytic amount of copper. See, e.g., Tornoe, et al., (2002) *Org. Chem.* 67:3057-3064; and, Rostovtsev, et al., (2002) *Angew. Chem. Int. Ed.* 41:2596-2599. By introducing an azide moiety into a protein structure, for example, one is able to incorporate a functional group that is chemically inert to amines, sulfhydryls, carboxylic acids, hydroxyl groups found in proteins, but that also reacts smoothly and efficiently with an acetylene moiety to form a cycloaddition product. Importantly, in the absence of the acetylene moiety, the azide remains chemically inert and unreactive in the presence of other protein side chains and under physiological conditions.

The present invention addresses, among other things, problems associated with the activity and production of antigen-binding polypeptides and fragments thereof, and in particular polypeptide small molecule conjugates, and also addresses the production of antigen-binding polypeptides and polypeptide small molecule conjugates with improved biological or pharmacological properties, such as improved therapeutic half-life.

BRIEF SUMMARY OF THE INVENTION

This invention provides anti-CD3 antibodies and conjugates thereof to folate. In some embodiments, the novel anti-CD3 antibodies of the present invention comprise one or more non-naturally encoded amino acids. In some embodiments, the anti-CD3 antibody comprises a complete antibody heavy chain. In some embodiments, the anti-CD3 antibody comprises a complete antibody light chain. In some embodiments, the anti-CD3 antibody comprises a variable region of an antibody light chain. In some embodiments, the anti-CD3 antibody comprises a variable region of an antibody heavy chain. In some embodiments, the anti-CD3 antibody comprises at least one CDR of an antibody light chain. In some embodiments, the anti-CD3 antibody comprises at least one CDR of a anti-CD3 antibodyantibody heavy chain. In some embodiments, the anti-CD3 antibody comprises at least one CDR of a light chain and at least one CDR of a heavy chain. In some embodiments, the anti-CD3 antibody comprises a Fab. In some embodiments, the anti-CD3 antibody comprises two or more Fab's. In some embodiments, the anti-CD3 antibody comprises a scFv. In some embodiments, the anti-CD3 antibody comprises two or more scFv. In some embodiments, the anti-CD3 antibody comprises a minibody. In some embodiments, the anti-CD3 antibody comprises two or more minibodies. In some embodiments, the anti-CD3 antibody comprises a diabody. In some embodiments, the anti-CD3 antibody comprises two or more diabodies. In some embodiments, the anti-CD3 antibody comprises a variable region of a light chain and a variable region of a heavy chain. In some embodiments, the anti-CD3 antibody comprises a complete light chain and a complete heavy chain. In some embodiments, the anti-CD3 antibody comprises one or more Fc domain or portion thereof. In some embodiments, the anti-CD3 antibody comprises a combination of any of the above embodiments. In some embodiments, the anti-CD3 antibody comprises a homodimer, heterodimer, homomultimer or heteromultimer of any of the above embodiments. In some embodiments, the anti-CD3 antibody comprises a polypeptide that binds to a binding partner wherein the binding partner comprises an antigen, a polypeptide, a nucleic acid molecule, a polymer, or other molecule or substance. In some embodiments, the anti-CD3 antibody is associated with a non-antibody scaffold molecule or substance.

In some embodiments, the anti-CD3 antibody comprises one or more post-translational modifications. In some embodiments, the anti-CD3 antibody is linked to a linker, polymer, or biologically active molecule. In some embodiments, the anti-CD3 antibody is linked to a bifunctional polymer, bifunctional linker, or at least one additional anti-CD3 antibody. In some embodiments, the anti-CD3 antibody is linked to a polypeptide that is not a anti-CD3 antibody. In some embodiments, an antigen-binding polypeptide comprising a non-naturally encoded amino acid is linked to one or more additional antigen-binding polypeptides which may also comprise a non-naturally encoded amino acid. In some embodiments, an antigen-binding polypeptide comprising a non-naturally encoded amino acid is linked to one or more polypeptide small molecule conjugates which may also comprise a non-naturally encoded amino acid. In some embodiments, a anti-CD3 antibody comprising a non-naturally encoded amino acid is linked to one or more additional antigen-binding polypeptides which may also comprise a non-naturally encoded amino acid.

In some embodiments, the non-naturally encoded amino acid is linked to a water soluble polymer. In some embodiments, the water soluble polymer comprises a poly(ethylene glycol) moiety. In some embodiments, the poly(ethylene glycol) molecule is a bifunctional polymer. In some embodiments, the bifunctional polymer is linked to a second polypeptide. In some embodiments, the second polypeptide is an antigen-binding polypeptide. In some embodiments, the second polypeptide is a anti-CD3 antibody.

In some embodiments the amino acid substitutions in the anti-CD3 antibody may be with naturally occurring or non-naturally occurring amino acids, provided that at least one substitution is with a non-naturally encoded amino acid.

In some embodiments, the non-naturally encoded amino acid comprises a carbonyl group, an acetyl group, an aminooxy group, a hydrazine group, a hydrazide group, a semicarbazide group, an azide group, or an alkyne group.

In some embodiments, the poly(ethylene glycol) molecule has a molecular weight of between about 0.1 kDa and about 100 kDa. In some embodiments, the poly(ethylene glycol) molecule has a molecular weight of between 0.1 kDa and 50 kDa.

In some embodiments, the poly(ethylene glycol) molecule is a branched polymer. In some embodiments, each branch of the poly(ethylene glycol) branched polymer has a molecular weight of between 1 kDa and 100 kDa, or between 1 kDa and 50 kDa.

The present invention also provides an anti-CD3 antibody polypeptide comprising a linker, polymer, or biologically active molecule that is attached to one or more non-naturally encoded amino acid wherein said non-naturally encoded amino acid is ribosomally incorporated into the polypeptide at pre-selected sites.

BRIEF DESCRIPTION OF THE DRAWINGS

FIG. 1 (A) is a graph of the dose-dependent T cell-mediated cytotoxicity with KB (FR+), OV-90 (FR+) and CAKI-1 (FR−) cells treated with anti-CD3 Fab-folate in the presence of activated human PBMCs (ratio 1:10 of target: effector cells). Increasing concentrations of anti-CD3 Fab-folate or unconjugated anti-CD3 Fab were incubated with target cells for 12-24 h at 37° C. and 5% CO2. Cytotoxicity was quantitated by measuring LDH levels released from lysed cells according to manufacturer's protocol (Cytotox 96 nonradioactive cytotoxicity assay, Promega). FIG. 1(B) shows SKOV-3 cells maintained in folate-free RPMI-1640 medium supplemented with 10% FBS for at least three passages before being seeded in a 48-well cell culture plate and allowed to attach to plate, after which activated human PBMCs (ratio 1:10 of target: effector cells) were added. Anti-CD3 Fab or anti-CD3 Fab-folate were diluted in folate-free medium and added at the indicated concentration and the co-culture was incubated for 16 hours. Images were taken with a 25x objective microscope.

FIG. 2(A) shows tumor volumes from this experiment. The tumor volume showed a rapid increase in PBS treated mice with a doubling time of approximately 5 days. In contrast, tumors in mice treated with anti-CD3 Fab-folate were barely detectable throughout the duration of the study. In a parallel study, mice were implanted with KB cells mixed with unactivated human PBMCs (ratio 1:100 of target: effector cells) and treated intravenously with 1.5 mg/kg of anti-CD3 Fab-folate or PBS daily for 10 days starting on the same day as tumor cell implantation. FIG. 2(B) shows tumor volumes from the 1:100 target:effector cell experiment. The rate of decrease of the tumors was higher in anti-CD3 Fab-folate treated mice. After day 35 of the study, the tumors in PBS treated mice steadily increased in volume while tumors in the anti-CD3 Fab-folate treated mice decreased to barely detectable levels indicating the engagement of cytotoxic T cells for the elimination of the tumors by the anti-CD3 Fab-folate conjugate even in the absence of activated T cells. FIG. 2(C) shows a graphical representation of the change in body weight in the mice from both treatment groups. FIG. 2(D) shows the serum concentration over time of rats in three test groups: those injected with 1 mg/kg anti-CD3Fab-folate; those injected with 5 mg/kg anti-CD3Fab-folate; and those injected with 1 mg/kg anti-CD3Fab. Serum was collected at regular intervals and analyzed by ELISA. The serum concentration decreased for both anti-CD3 Fab-folate and the corresponding unconjugated mutant anti-CD3 Fab at the same rate with a serum half-life of 60 mins.

FIG. 3(A) is a graphical representation of the binding of Folate-CF488 to KB cells (FR+) but not to A549 cells (FR−) analyzed by competition with free folate. Cells were incubated with media containing increasing concentrations of the conjugate and 100 nM folate for 30 mins at 4° C. and cell bound fluorescence was analyzed by flow cytometry. FIG. 3(B) is a graphical representation of the binding of anti-CD3 Fab-CF488 to Jurkat cells (CD3+) but not to KB cells (CD3−). Cells were incubated with increasing concentrations of the conjugate for 30 mins at 4° C. and binding was analyzed by flow cytometry.

In FIG. 4(A) the cells were labeled with DIO (green plasma membrane stain) and Propidium iodide was added to a final concentration of 1 µg/mL. Cytotoxicity was measured by flow cytometry. FIG. 4(B) shows a graphical representation of PBMCs that were washed off after 24 hrs and ATP content of KB cells was measured using Cell Titer Gla (Promega).

DEFINITIONS

Figure 1:
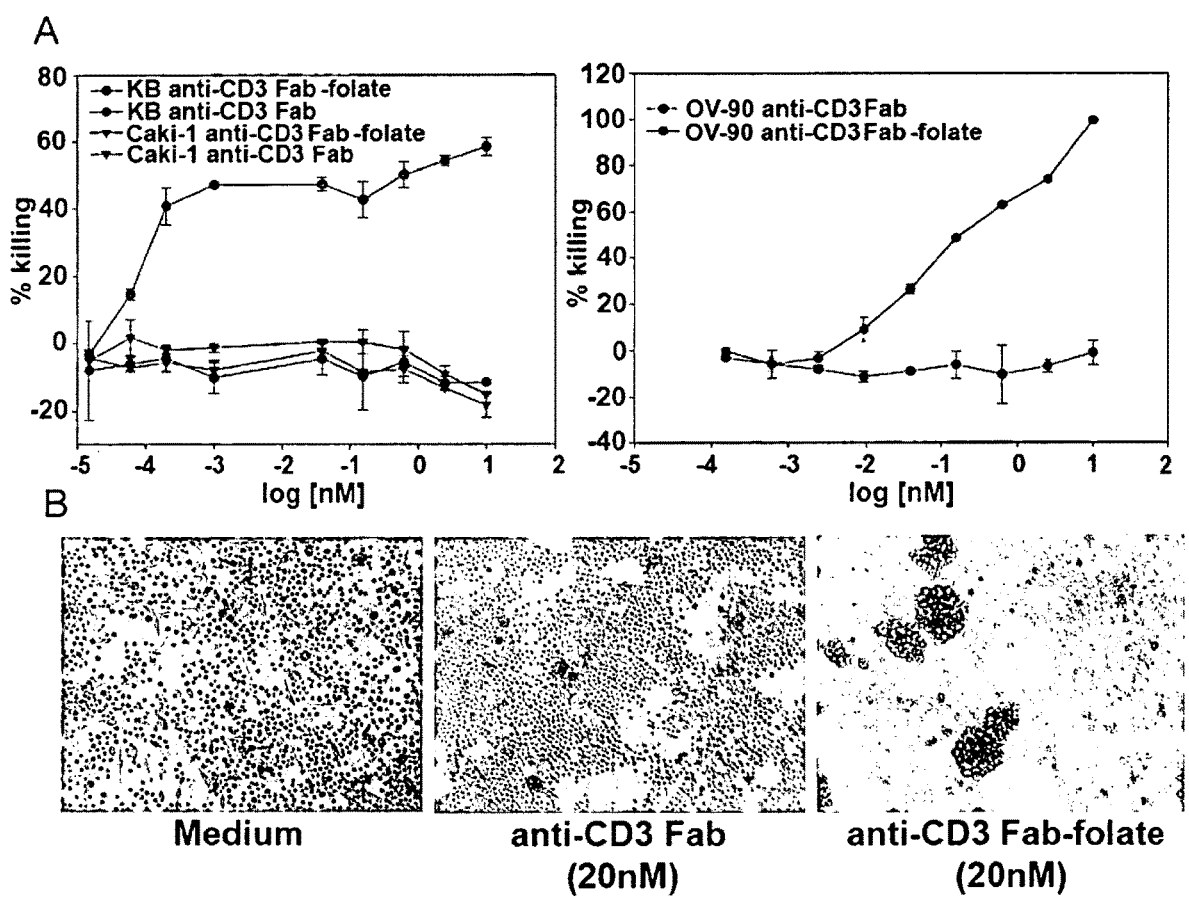
FIG. 1—Shows the T cell engagement of target cells and dose-dependent toxicity by anti-CD3 Fab-folate.

It is to be understood that this invention is not limited to the particular methodology, protocols, cell lines, constructs, and reagents described herein and as such may vary. It is also to be understood that the terminology used herein is for the purpose of describing particular embodiments only, and is not intended to limit the scope of the present invention, which will be limited only by the appended claims.

As used herein and in the appended claims, the singular forms "a," "an," and "the" include plural reference unless the context clearly indicates otherwise. Thus, for example, reference to an "polypeptide small molecule conjugate" or "anti-CD3 antibody" is a reference to one or more such proteins and includes equivalents thereof known to those skilled in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention or for any other reason.

The term "substantially purified" refers to a anti-CD3 antibody that may be substantially or essentially free of components that normally accompany or interact with the protein as found in its naturally occurring environment, i.e., a native cell, or host cell in the case of recombinantly produced anti-CD3 antibody, anti-CD3 antibody that may be substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the anti-CD3 antibody or variant thereof is recombinantly produced by the host cells, the protein may be present at about 30%, about 25%, about 20%, about 15%, about 10%, about 5%, about 4%, about 3%, about 2%, or about 1% or less of the dry weight of the cells. When the anti-CD3 antibody or variant thereof is recombinantly produced by the host cells, the protein may be present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. Thus, "substantially purified" anti-CD3 antibody as produced by the methods of the present invention may have a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

Antibodies are proteins, which exhibit binding specificity to a specific antigen. Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains.

The term "variable" refers to the fact that certain portions of the variable domains differ extensively in sequence among antibodies and are responsible for the binding specificity of each particular antibody for its particular antigen. However, the variability is not evenly distributed through the variable domains of antibodies. It is concentrated in three segments called Complementarity Determining Regions (CDRs) both in the light chain and the heavy chain variable domains. The more highly conserved portions of the variable domains are called the framework regions (FR). The variable domains of native heavy and light chains each comprise four FR regions, largely adopting a β-sheet configuration, connected by three or four CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat et al., Sequences of Proteins of Immunological Interest, 5th Ed. Public Health Service, National Institutes of Health, Bethesda, MD (1991)).

The constant domains are not involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgD, IgE, IgG and IgM, and several of these may be further divided into subclasses (isotypes), e.g. IgG1, IgG2, IgG3, and IgG4; IgA1 and IgA2. The heavy chain constant regions that correspond to the different classes of immunoglobulins are called α, δ, ε, γ and μ, respectively. Of the various human immunoglobulin classes, only human IgG1, IgG2, IgG3 and IgM are known to activate complement.

In vivo, affinity maturation of antibodies is driven by antigen selection of higher affinity antibody variants which are made primarily by somatic hypermutagenesis. A "repertoire shift" also often occurs in which the predominant gatinline genes of the secondary or tertiary response are seen to differ from those of the primary or secondary response.

The affinity maturation process of the immune system may be replicated by introducing mutations into antibody genes in vitro and using affinity selection to isolate mutants with improved affinity. Such mutant antibodies can be displayed on the surface of filamentous bacteriophage or microorganisms such as yeast, and antibodies can be selected by their affinity for antigen or by their kinetics of dissociation (off-rate) from antigen. Hawkins et al, J. Mol. Biol. 226:889-896 (1992). CDR walking mutagenesis has been employed to affinity mature human antibodies which bind the human envelope glycoprotein gp120 of human immunodeficiency virus type 1 (HIV-1) (Barbas III et al. PNAS (USA) 91: 3809-3813 (1994); and Yang et al. J. Mol. Biol. 254:392-403 (1995)); and an anti-c-erbB-2 single chain Fv fragment (Schicr et al. J. Mol. Biol. 263:551567 (1996)). Antibody chain shuffling and CDR mutagenesis were used to affinity mature a high-affinity human antibody directed against the third hypervariable loop of HIV (Thompson et al. J. Mol. Biol. 256:77-88 (1996)). Balint and Larrick Gene 137:109-118 (1993) describe a computer-assisted oligodeoxyribonucleotide-directed scanning mutagenesis whereby all CDRs of a variable region gene are simultaneously and thoroughly searched for improved variants. An αvβ3-specific humanized antibody was affinity matured using an initial limited mutagenesis strategy in which every position of all six CDRs was mutated followed by the expression and screening of a combinatorial library including the highest affinity mutants (Wu et al. PNAS (USA) 95: 6037-6-42 (1998)). Phage displayed antibodies are reviewed in Chiswell and McCafferty TIBTECH 10:80-84 (1992); and Rader and Barbas III Current Opinion in Biotech. 8:503-508 (1997). In each case where mutant antibodies with improved affinity compared to a parent antibody are reported in the above references, the mutant antibody has amino acid substitutions in a CDR.

By "affinity maturation" herein is meant the process of enhancing the affinity of an antibody for its antigen. Methods for affinity maturation include but are not limited to computational screening methods and experimental methods.

By "antibody" herein is meant a protein consisting of one or more polypeptides substantially encoded by all or part of the antibody genes. The immunoglobulin genes include, but are not limited to, the kappa, lambda, alpha, gamma (IgG1, IgG2, IgG3, and IgG4), delta, epsilon and mu constant region genes, as well as the myriad immunoglobulin variable region genes. Antibody herein is meant to include full-length antibodies and antibody fragments, and include antibodies that exist naturally in any organism or are engineered (e.g. are variants).

By "antibody fragment" is meant any form of an antibody other than the full-length form. Antibody fragments herein include antibodies that are smaller components that exist within full-length antibodies, and antibodies that have been engineered. Antibody fragments include but are not limited to Fv, Fc, Fab, and (Fab')$_2$, single chain Fv (scFv), diabodies, triabodies, tetrabodies, bifunctional hybrid antibodies, CDR1, CDR2, CDR3, combinations of CDR's, variable regions, framework regions, constant regions, and the like (Maynard & Georgiou, 2000, Annu. Rev. Biomed. Eng. 2:339-76; Hudson, 1998, Curr. Opin. Biotechnol. 9:395-402).

By "computational screening method" herein is meant any method for designing one or more mutations in a protein, wherein said method utilizes a computer to evaluate the energies of the interactions of potential amino acid side chain substitutions with each other and/or with the rest of the protein.

By "Fc" herein is meant the portions of an antibody that are comprised of immunoglobulin domains Cγ2 and Cγ3 (Cγ2 and Cγ3). Fc may also include any residues which exist in the N-terminal hinge between Cγ2 and Cγ1 (Cγ1). Fc may refer to this region in isolation, or this region in the context of an antibody or antibody fragment. Fc also includes any modified forms of Fc, including but not limited to the native monomer, the native dimer (disulfide bond linked), modified dimers (disulfide and/or non-covalently linked), and modified monomers (i.e., derivatives).

By "full-length antibody" herein is meant the structure that constitutes the natural biological form of an antibody H and/or L chain. In most mammals, including humans and mice, this form is a tetramer and consists of two identical pairs of two immunoglobulin chains, each pair having one light and one heavy chain, each light chain comprising immunoglobulin domains $V_L$ and $C_L$, and each heavy chain comprising immunoglobulin domains $V_H$, Cγ1, Cγ2, and Cγ3. In each pair, the light and heavy chain variable regions ($V_L$ and $V_H$) are together responsible for binding to an antigen, and the constant regions ($C_L$, Cγ1, Cγ2, and Cγ3, particularly Cγ2, and Cγ3) are responsible for antibody effector functions. In some mammals, for example in camels and llamas, full-length antibodies may consist of only two heavy chains, each heavy chain comprising immunoglobulin domains $V_H$, Cγ2, and Cγ3.

By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full-length antibodies, antibody fragments, and individual immunoglobulin domains including but not limited to $V_H$, Cγ1, Cγ2, Cγ3, $V_L$, and $C_L$.

By "immunoglobulin (Ig) domain" herein is meant a protein domain consisting of a polypeptide substantially encoded by an immunoglobulin gene, Ig domains include but are not limited to $V_H$, Cγ1, Cγ2, Cγ3, $V_L$, and $C_L$ as is shown in FIG. 1.

By "variant protein sequence" as used herein is meant a protein sequence that has one or more residues that differ in amino acid identity from another similar protein sequence. Said similar protein sequence may be the natural wild type protein sequence, or another variant of the wild type sequence. In general, a starting sequence is referred to as a "parent" sequence, and may either be a wild type or variant sequence. For example, preferred embodiments of the present invention may utilize humanized parent sequences upon which computational analyses are done to make variants.

By "variable region" of an antibody herein is meant a polypeptide or polypeptides composed of the $V_H$ immunoglobulin domain, the $V_L$ immunoglobulin domains, or the $V_H$ and $V_L$ immunoglobulin domains as is shown in FIG. 1 (including variants). Variable region may refer to this or these polypeptides in isolation, as an Fv fragment, as a scFv fragment, as this region in the context of a larger antibody fragment, or as this region in the context of a full-length antibody or an alternative, non-antibody scaffold molecule.

The present invention may be applied to antibodies obtained from a wide range of sources. The antibody may be substantially encoded by an antibody gene or antibody genes from any organism, including but not limited to humans, mice, rats, rabbits, camels, llamas, dromedaries, monkeys, particularly mammals and particularly human and particularly mice and rats. In one embodiment, the antibody may be fully human, obtained for example from a patient or subject, by using transgenic mice or other animals (Bruggemann & Taussig, 1997, Curr. Opin. Biotechnol. 8:455-458) or human antibody libraries coupled with selection methods (Griffiths & Duncan, 1998, Curr. Opin, Biotechnol. 9:102-108). The antibody may be from any source, including artificial or naturally occurring. For example the present invention may utilize an engineered antibody, including but not limited to chimeric antibodies and humanized antibodies (Clark, 2000, Immunol. Today 21:397-402) or derived from a combinatorial library. In addition, the antibody being optimized may be an engineered variant of an antibody that is substantially encoded by one or more natural antibody genes. For example, in one embodiment the antibody being optimized is an antibody that has been identified by affinity maturation.

With respect to anti-CD3 antibody's of the invention, the term "antigenically specific" or "specifically binds" refers to anti-CD3 antibody's that bind to one or more epitopes of an antigen or binding partner of interest, but which do not substantially recognize and bind other molecules in a sample containing a mixed population of antigens.

The term "bispecific anti-CD3 antibody" or "multispecific anti-CD3 antibody" as used herein refers to a anti-CD3 antibody comprising two or more antigen-binding sites or binding partner binding sites, a first binding site having affinity for a first antigen or epitope and a second binding site having binding affinity for a second antigen or epitope distinct from the first.

The term "epitope" as used herein refers to a site on an antigen or binding partner that is recognized by anti-CD3 antibody. An epitope may be a linear or conformationally formed sequence or shape of amino acids, if the antigen comprises a polypeptide. An epitope may also be any location on any type of antigen where a anti-CD3 antibody binds to the antigen.

As used herein, "antigen-binding polypeptide" or "anti-CD3 antibody" shall include those polypeptides and proteins that have at least the biological activity of specific binding to a particular binding partner such as antigen, as well as anti-CD3 antibody analogs, anti-CD3 antibody isoforms, anti-CD3 antibody mimetics, anti-CD3 antibody fragments, hybrid anti-CD3 antibody proteins, fusion proteins, oligomers and multimers, homologues, glycosylation pattern variants, and muteins, thereof, regardless of the biological activity of same, and further regardless of the method of synthesis or manufacture thereof including, but not limited to, recombinant (whether produced from cDNA, genomic DNA, synthetic DNA or other form of nucleic acid), in vitro, in vivo, by microinjection of nucleic acid molecules, synthetic, transgenic, and gene activated methods. Specific examples of anti-CD3 antibody include, but are not limited to, antibody molecules, heavy chain, light chain, variable region, CDR, Fab, scFv, alternative scaffold non-antibody molecules, ligands, receptors, peptides, or any amino acid sequence that binds to an antigen.

The term "anti-CD3 antibody" or "antigen-binding polypeptide" refers to a anti-CD3 antibody as described above, as well as a polypeptide that retains at least one biological activity of a naturally-occurring antibody, including but not limited to, activities other than antigen binding. Activities other than antigen binding include, but are not limited to, any one or more of the activities associated with the Fc.

Antigen-binding polypeptides include the pharmaceutically acceptable salts and prodrugs, and prodrugs of the salts, polymorphs, hydrates, solvates, biologically-active fragments, biologically-active variants and stereoisomers of the naturally-occurring huma anti-CD3 antibody as well as agonist, mimetic, and antagonist variants of the naturally-occurring huma anti-CD3 antibody and polypeptide fusions thereof. Fusions comprising additional amino acids at the amino terminus, carboxyl terminus, or both, are encompassed by the term "antigen-binding polypeptide." Exemplary fusions include, but are not limited to, e.g., methionyl anti-CD3 antibody in which a methionine is linked to the N-terminus of anti-CD3 antibody resulting from the recombinant expression, fusions for the purpose of purification (including but not limited to, to poly-histidine or affinity epitopes), fusions for the purpose of linking anti-CD3 antibody's to other biologically active molecules, fusions with serum albumin binding peptides, and fusions with serum proteins such as serum albumin.

The term "antigen" or "binding partner" refers to a substance that is the target for the binding activity exhibited by the anti-CD3 antibody. Virtually any substance may be an antigen or binding partner for a anti-CD3 antibody Bispecific antibodies of the present invention include anti-CD3 bispecific antibodies with a humanized SP34 antibody or antibody fragment. In some embodiments of the present invention the humanized SP34 antibody has a non-naturally encoded amino acid at position 160 of the heavy chain. In some embodiments of the present invention the humanized SP34 antibody has a non-naturally encoded amino acid at position 172 of the light chain. In some embodiments of the present invention the humanized SP34 antibody has a non-naturally encoded amino acid at position 157 of the light chain. In some embodiments of the present invention the humanized SP34 antibody has a non-naturally encoded amino acid at position 129 of the heavy chain. In some embodiments of the present invention the humanized SP34 antibody has a non-naturally encoded amino acid at position 129 of the heavy chain and position 172 of the light chain.

In some embodiments, the present invention encompasses a humanized SP34 antibody comprising a non-naturally encoded amino acid at position 204 of the heavy chain. In some embodiments of the present invention the humanized SP34 antibody has a non-naturally encoded amino acid at position 210 of the heavy chain. In some embodiments of the present invention the humanized SP34 antibody has a non-naturally encoded amino acid at position 191 of the heavy chain. In some embodiments of the present invention the humanized SP34 antibody has a non-naturally encoded amino acid at position 187 of the heavy chain. In some embodiments of the present invention the humanized SP34 antibody has a non-naturally encoded amino acid at position 133 of the heavy chain. In some embodiments of the present invention the humanized SP34 antibody has a non-naturally encoded amino acid at position 114 of the heavy chain. In some embodiments of the present invention the humanized SP34 antibody has a non-naturally encoded amino acid at position 115 of the heavy chain. In some embodiments of the present invention the humanized SP34 antibody has a non-naturally encoded amino acid at position 111 of the light chain. In some embodiments of the present invention the humanized SP34 antibody has a non-naturally encoded amino acid at position 115 of the light chain. In some embodiments of the present invention the humanized SP34 antibody has a non-naturally encoded amino acid at position 204 of the light chain. In some embodiments of the present invention the humanized SP34 antibody has a non-naturally encoded amino acid at position 191 of the light chain. In some embodiments of the present invention the humanized SP34 antibody has a non-naturally encoded amino acid at position 193 of the light chain. In some embodiments of the present invention the humanized SP34 antibody has a non-naturally encoded amino acid at position 186 of the light chain. In some embodiments of the present invention the humanized SP34 antibody has two of the aforementioned amino acid changes. In some embodiments of the present invention the humanized SP34 antibody has two or more of the aforementioned amino acid changes.

Bispecific antibodies of the present invention include anti-CD3 bispecific antibodies with a humanized SP34 antibody or antibody fragment. In some embodiments of the present invention the humanized SP34 antibody has a non-naturally encoded amino acid substituted for position 160Thr of the heavy chain. In some embodiments of the present invention the humanized SP34 antibody has a non-naturally encoded amino acid substituted for position 172Lys of the light chain. In some embodiments of the present invention the humanized SP34 antibody has a non-naturally encoded amino acid substituted for position 157Leu of the light chain. In some embodiments of the present invention the humanized SP34 antibody has a non-naturally encoded amino acid substituted for position 129Lys of the heavy chain. In some embodiments of the present invention the humanized SP34 antibody has a non-naturally encoded amino acid substituted for position 129Lys of the heavy chain and position 172Lys of the light chain. In some embodiments of the present invention the humanized SP34 antibody has a non-naturally encoded amino acid substituted for position 129Lys of the heavy chain and position 157Leu of the light chain.

In some embodiments of the present invention the humanized SP34 antibody has a non-naturally encoded amino acid substituted for position 204Asn of the heavy chain. In some embodiments of the present invention the humanized SP34 antibody has a non-naturally encoded amino acid substituted for position 210Lys of the heavy chain. In some embodiments of the present invention the humanized SP34 antibody has a non-naturally encoded amino acid substituted for position 191Thr of the heavy chain. In some embodiments of the present invention the humanized SP34 antibody has a non-naturally encoded amino acid substituted for position 187Ser of the heavy chain. In some embodiments of the present invention the humanized SP34 antibody has a non-naturally encoded amino acid substituted for position 133Gly of the heavy chain. In some embodiments of the present invention the humanized SP34 antibody has a non-naturally encoded amino acid substituted for position 114Ala of the heavy chain. In some embodiments of the present invention the humanized SP34 antibody has a non-naturally encoded amino acid substituted for position 115Ser of the heavy chain. In some embodiments of the present invention the humanized SP34 antibody has a non-naturally encoded amino acid substituted for position 111Arg of the light chain. In some embodiments of the present invention the humanized SP34 antibody has a non-naturally encoded amino acid substituted for position 115Ala of the light chain. In some embodiments of the present invention the humanized SP34 antibody has a non-naturally encoded amino acid substituted for position 204Leu of the light chain. In some embodiments of the present invention the humanized SP34 antibody has a non-naturally encoded amino acid substituted for position 191Lys of the light chain. In some embodiments of the present invention the humanized SP34 antibody has a non-naturally encoded amino acid substituted for position 193Lys of the light chain. In some embodiments of the present invention the humanized SP34 antibody has a non-naturally encoded amino acid substituted for position 186Lys of the light chain.

Bispecific antibodies of the present invention include anti-CD3 Fab-folate bispecific antibodies with a humanized SP34 antibody or antibody fragment conjugated to folate. In some embodiments of the present invention the humanized SP34 antibody is conjugated to folate at position 160Thr of the heavy chain. In some embodiments of the present invention the humanized SP34 antibody is conjugated to folate at position 172Lys of the light chain. In some embodiments of the present invention the humanized SP34 antibody is conjugated to folate at position 157Leu of the light chain. In some embodiments of the present invention the humanized SP34 antibody is conjugated to folate at position 129Lys of the heavy chain. In some embodiments of the present invention the humanized SP34 antibody is conjugated to folate at position 129Lys of the heavy chain and position 172Lys of the light chain. In some embodiments of the present invention the humanized SP34 antibody is conjugated to folate at position 129Lys of the heavy chain and position 157Leu of the light chain.

In some embodiments of the present invention the humanized SP34 antibody is conjugated to folate at position 204Asn of the heavy chain. In some embodiments of the present invention the humanized SP34 antibody is conjugated to folate at position 210Lys of the heavy chain. In some embodiments of the present invention the humanized SP34 antibody is conjugated to folate at position 191Thr of the heavy chain. In some embodiments of the present invention the humanized SP34 antibody is conjugated to folate at position 187Ser of the heavy chain. In some embodiments of the present invention the humanized SP34 antibody is conjugated to folate at position 133Gly of the heavy chain. In some embodiments of the present invention the humanized SP34 antibody is conjugated to folate at position 114Ala of the heavy chain. In some embodiments of the present invention the humanized SP34 antibody is conjugated to folate at 115Ser of the heavy chain. In some embodiments of the present invention the humanized SP34 antibody is conjugated to folate at position 111Arg of the light chain. In some embodiments of the present invention the humanized SP34 antibody is conjugated to folate at position 115Ala of the light chain. In some embodiments of the present invention the humanized SP34 antibody is conjugated to folate at position 204Leu of the light chain. In some embodiments of the present invention the humanized SP34 antibody is conjugated to folate at position 191Lys of the light chain. In some embodiments of the present invention the humanized SP34 antibody is conjugated to folate at position 193Lys of the light chain. In some embodiments of the present invention the humanized SP34 antibody is conjugated to folate at position 186Lys of the light chain.

Various references disclose modification of polypeptides by polymer conjugation or glycosylation. The term "anti-CD3 antibody" or "antigen-binding polypeptide" includes, but is not limited to, polypeptides conjugated to a polymer such as PEG and may be comprised of one or more additional derivitizations of cysteine, lysine, N or C-terminal amino acids, or other residues. In addition, the anti-CD3 antibody may comprise a linker, polymer or biologically active molecule, wherein the amino acid to which the linker, polymer, or biologically active molecule is conjugated may be a non-natural amino acid according to the present invention, or may be conjugated to a naturally encoded amino acid utilizing techniques known in the art such as coupling to lysine or cysteine. U.S. Pat. No. 4,904,584 discloses PEGylated lysine depleted polypeptides, wherein at least one lysine residue has been deleted or replaced with any other amino acid residue. WO 99/67291 discloses a process for conjugating a protein with PEG, wherein at least one amino acid residue on the protein is deleted and the protein is contacted with PEG under conditions sufficient to achieve conjugation to the protein. WO 99/03887 discloses PEGylated variants of polypeptides belonging to the growth hormone superfamily, wherein a cysteine residue has been substituted with a non-essential amino acid residue located in a specified region of the polypeptide, WO 00/26354 discloses a method of producing a glycosylated polypeptide variant with reduced allergenicity, which as compared to a corresponding parent polypeptide comprises at least one additional glycosylation site.

The term "antigen-binding polypeptide" also includes glycosylated anti-CD3 antibodies, such as but not limited to, polypeptides glycosylated at any amino acid position, N-linked or O-linked glycosylated forms of the polypeptide. Variants containing single nucleotide changes are also considered as biologically active variants of anti-CD3 antibody. In addition, splice variants are also included. The term "antigen-binding polypeptide" also includes anti-CD3 antibody heterodimers, homodimers, heteromultimers, or homomultimers of any one or more anti-CD3 antibody or any other polypeptide, protein, carbohydrate, polymer, small molecule, linker, ligand, or other biologically active molecule of any type, linked by chemical means or expressed as a fusion protein, as well as polypeptide analogues containing, for example, specific deletions or other modifications yet maintain biological activity.

In some embodiments, the antigen-binding polypeptides further comprise an addition, substitution or deletion that modulates biological activity of the anti-CD3 antibody. For example, the additions, substitutions or deletions may modulate one or more properties or activities of the anti-CD3 antibody, including but not limited to, modulating affinity for the antigen, modulate (including but not limited to, increases or decreases) antigen conformational or other secondary, tertiary or quaternary structural changes, stabilize antigen conformational or other secondary, tertiary or quaternary structural changes, induce or cause antigen conformational or other secondary, tertiary or quaternary structural changes, modulate circulating half-life, modulate therapeutic half-life, modulate stability of the polypeptide, modulate dose, modulate release or bio-availability, facilitate purification, or improve or alter a particular route of administration. Similarly, antigen-binding polypeptides may comprise protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification or other traits of the polypeptide.

The term "antigen-binding polypeptide" also encompasses anti-CD3 antibody homodimers, heterodirners, homornultimers, and heteromultimers that are linked, including but not limited to those linked directly via non-naturally encoded amino acid side chains, either to the same or different non-naturally encoded amino acid side chains, to naturally-encoded amino acid side chains, as fusions, or indirectly via a linker. Exemplary linkers include but are not limited to, small organic compounds, water soluble polymers of a variety of lengths such as poly(ethylene glycol) or polydextran, or polypeptides of various lengths.

Those of skill in the art will appreciate that amino acid positions corresponding to positions in a particular antigen-binding polypeptide sequence can be readily identified in a fragment of the antigen-binding polypeptide or related antigen-binding polypeptide, etc. For example, sequence alignment programs such as BLAST can be used to align and identify a particular position in a protein that corresponds with a position in a related sequence.

The term "antigen-binding polypeptide" encompasses antigen-binding polypeptides comprising one or more amino acid substitutions, additions or deletions. Antigen-binding polypeptides of the present invention may be comprised of modifications with one or more natural amino acids in conjunction with one or more non-natural amino acid modification. Exemplary substitutions in a wide variety of amino acid positions in naturally-occurring anti-CD3 antibody polypeptides have been described, including but not limited to substitutions that modulate one or more of the biological activities of the antigen-binding polypeptide, such as but not limited to, increase agonist activity, increase solubility of the polypeptide, convert the polypeptide into an antagonist, etc. and are encompassed by the term "anti-CD3 antibody."

A "non-naturally encoded amino acid" refers to an amino acid that is not one of the 20 common amino acids or pyrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

An "amino terminus modification group" refers to any molecule that can be attached to the amino terminus of a polypeptide. Similarly, a "carboxy terminus modification group" refers to any molecule that can be attached to the carboxy terminus of a polypeptide. Terminus modification groups include, but are not limited to, various water soluble polymers, peptides or proteins such as serum albumin, or other moieties that increase serum half-life of peptides.

The terms "functional group", "active moiety", "activating group", "leaving group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules.

The term "linkage" or "linker" is used herein to refer to groups or bonds that normally are formed as the result of a chemical reaction and typically are covalent linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide. Branched linkers may be used in antigen-binding polypeptides of the invention.

The term "biologically active molecule", "biologically active moiety" or "biologically active agent" when used herein means any substance which can affect any physical or biochemical properties of a biological system, pathway, molecule, or interaction relating to an organism, including but not limited to, viruses, bacteria, bacteriophage, transposon, prion, insects, fungi, plants, animals, and humans. In particular, as used herein, biologically active molecules include, but are not limited to, any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, hard drugs, soft drugs, dyes, lipids, nucleosides, oligonucleotides, toxins, cells, viruses, liposomes, microparticles and micelles. Classes of biologically active agents that are suitable for use with the invention include, but are not limited to, drugs, prodrugs, radionuclides, imaging agents, polymers, antibiotics, fungicides, anti-viral agents, anti-inflammatory agents, anti-tumor agents, cardiovascular agents, anti-anxiety agents, hormones, growth factors, steroidal agents, microbially derived toxins, and the like.

The anti-CD3 antibodies of the invention may be conjugated to molecules such as PEG to improve in vivo delivery and pharmacokinetic profiles. Leong et al, describe site-specific PEGylation of a Fab' fragment of an anti-IL-8 antibody with a decreased clearance rate over the non-PEGylated form and little or no loss of antigen binding activity (Leong, S. R. et al. (2001) Cytokine 16:106-119).

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. The length of the linker may be predetermined or selected depending upon a desired spatial relationship between the anti-CD3 antibody and the molecule linked to it. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an anti-CD3 antibody or other polypeptide.

A "bifunctional polymer" refers to a polymer comprising two discrete functional groups that are capable of reacting specifically with other moieties (including but not limited to, amino acid side groups) to form covalent or non-covalent linkages. A bifunctional linker having one functional group reactive with a group on a particular biologically active component, and another group reactive with a group on a second biological component, may be used to form a conjugate that includes the first biologically active component, the bifunctional linker and the second biologically active component. Many procedures and linker molecules for attachment of various compounds to peptides are known. See, e.g., European Patent Application No. 188,256; U.S. Pat. Nos. 4,671,958, 4,659,839, 4,414,148, 4,699,784; 4,680,338; 4,569,789; and 4,589,071 which are incorporated by reference herein. A "multi-functional polymer" refers to a polymer comprising two or more discrete functional groups that are capable of reacting specifically with other moieties (including but not limited to, amino acid side groups) to form covalent or non-covalent linkages. A bi-functional polymer or multi-functional polymer may be any desired molecular length or molecular weight, and may be selected to provide a particular desired spacing or conformation between one of molecules linked to the anti-CD3 antibody.

As used herein, the term "water soluble polymer" refers to any polymer that is soluble in aqueous solvents. Linkage of water soluble polymers to anti-CD3 antibody can result in changes including, but not limited to, increased or modulated serum half-life, or increased or modulated therapeutic half-life relative to the unmodified form, modulated immunogenicity, modulated physical association characteristics such as aggregation and multimer formation, altered receptor binding and altered receptor dimerization or multimerization. The water soluble polymer may or may not have its own biological activity, and may be utilized as a linker for attaching a anti-CD3 antibody to other substances, including but not limited to one or more anti-CD3 antibody's, or one or more biologically active molecules. Suitable polymers include, but are not limited to, polyethylene glycol, polyethylene glycol propionaldehyde, mono C1-C10 alkoxy or aryloxy derivatives thereof (described in U.S. Pat. No. 5,252,714 which is incorporated by reference herein), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof. Examples of such water soluble polymers include, but are not limited to, polyethylene glycol and serum albumin.

As used herein, the term "polyalkylene glycol" or "poly (alkene glycol)" refers to polyethylene glycol (poly(ethylene glycol)), polypropylene glycol, polybutylene glycol, and derivatives thereof. The term "polyalkylene glycol" encompasses both linear and branched polymers and average molecular weights of between 0.1 kDa and 100 kDa. Other exemplary embodiments are listed, for example, in commercial supplier catalogs, such as Shearwater Corporation's catalog "Polyethylene Glycol and Derivatives for Biomedical Applications" (2001).

As used herein, the term "modulated serum half-life" means the positive or negative change in circulating half-life of a modified anti-CD3 antibody relative to its non-modified form. Serum half-life is measured by taking blood samples at various time points after administration of anti-CD3 antibody, and determining the concentration of that molecule in each sample. Correlation of the scrum concentration with time allows calculation of the serum half-life. Increased serum half-life desirably has at least about two-fold, but a smaller increase may be useful, for example where it enables a satisfactory dosing regimen or avoids a toxic effect. In some embodiments, the increase is at least about three-fold, at least about five-fold, or at least about ten-fold.

The term "modulated therapeutic half-life" as used herein means the positive or negative change in the half-life of the therapeutically effective amount of a anti-CD3 antibody or anti-CD3 antibody comprising a modified biologically active molecule, relative to its non-modified form. Therapeutic half-life is measured by measuring pharmacokinetic and/or phaiinacodynamic properties of the molecule at various time points after administration. Increased therapeutic half-life desirably enables a particular beneficial dosing regimen, a particular beneficial total dose, or avoids an undesired effect. In some embodiments, the increased therapeutic half-life results from increased potency, increased or decreased binding of the modified molecule to its target, or an increase or decrease in another parameter or mechanism of action of the non-modified molecule.

The term "isolated," when applied to a nucleic acid or protein, denotes that the nucleic acid or protein is substantially free of other cellular components with which it is associated in the natural state. It can be in a homogeneous state. Isolated substances can be in either a dry or semi-dry state, or in solution, including but not limited to, an aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to substantially one band in an electrophoretic gel. Particularly, it means that the nucleic acid or protein is at least 85% pure, at least 90% pure, at least 95% pure, at least 99% or greater pure.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res, 19:5081 (1991); Ohtsuka et al., J. Biol. Chem. 260:2605-2608 (1985); and Cassol et al. (1992); Rossolini et al., Mol. Cell. Probes 8:91-98 (1994)).

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins (i.e., antigens), wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, i.e., an at carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-TUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins: Structures and Molecular Properties* (W H Freeman & Co.; 2nd edition (December 1993)

The term "subject" as used herein, refers to an animal, preferably a mammal, most preferably a human, who is the object of treatment, observation or experiment.

The twin "effective amount" as used herein refers to that amount of the (modified) non-natural amino acid polypeptide being administered which will relieve to some extent one or more of the symptoms of the disease, condition or disorder being treated. Compositions containing the (modified) non-natural amino acid polypeptide described herein can be administered for prophylactic, enhancing, and/or therapeutic treatments.

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in a patient, amounts effective for this use will depend on the severity and course of the disease, disorder or condition, previous therapy, the patient's health status and response to the drugs, and the judgment of the treating physician.

The term "modified," as used herein refers to the presence of a post-translational modification on a polypeptide. The form "(modified)" term means that the polypeptides being discussed are optionally modified, that is, the polypeptides under discussion can be modified or unmodified.

The term "post-translationally modified" and "modified" refers to any modification of a natural or non-natural amino acid that occurs to such an amino acid after it has been incorporated into a polypeptide chain. The term encompasses, by way of example only, co-translational in vivo modifications, post-translational in vivo modifications, and post-translational in vitro modifications.

In therapeutic applications, compositions containing the (modified) non-natural amino acid polypeptide are administered to a patient already suffering from a disease, condition or disorder, in an amount sufficient to cure or at least partially arrest the symptoms of the disease, disorder or condition. Such an amount is defined to be a "therapeutically effective amount," and will depend on the severity and course of the disease, disorder or condition, previous therapy, the patient's health status and response to the drugs, and the judgment of the treating physician. It is considered well within the skill of the art for one to determine such therapeutically effective amounts by routine experimentation (e,g., a dose escalation clinical trial).

The term "treating" is used to refer to either prophylactic and/or therapeutic treatments.

Unless otherwise indicated, conventional methods of mass spectroscopy, NMR, HPLC, protein chemistry, biochemistry, recombinant DNA techniques and pharmacology, within the skill of the art are employed.

DETAILED DESCRIPTION

Introduction

Anti-CD3 antibody molecules comprising at least one unnatural amino acid are provided in the invention. In certain embodiments of the invention, anti-CD3 antibody with at least one unnatural amino acid includes at least one post-translational modification. In one embodiment, the at least one post-translational modification comprises attachment of a molecule including but not limited to, a water-soluble polymer, a derivative of polyethylene glycol, a drug, a second protein or polypeptide or polypeptide analog, an antibody or antibody fragment, a biologically active agent, a small molecule, or any combination of the above or any other desirable compound or substance, comprising a second reactive group to at least one unnatural amino acid comprising a first reactive group utilizing chemistry methodology that is known to one of ordinary skill in the art to be suitable for the particular reactive groups. For example, the first reactive group is an alkynyl moiety (including but not limited to, in the unnatural amino acid p-propargyloxyphenylalanine, where the propargyl group is also sometimes referred to as an acetylene moiety) and the second reactive group is an azido moiety, and [3+2] cycloaddition chemistry methodologies are utilized. In another example, the first reactive group is the azido moiety (including but not limited to, in the unnatural amino acid p-azido-L-phenylalanine) and the second reactive group is the alkynyl moiety. In certain embodiments of the modified anti-CD3 antibody polypeptide of the present invention, at least one unnatural amino acid (including but not limited to, unnatural amino acid containing a keto functional group) comprising at least one post-translational modification, is used where the at least one post-translational modification comprises a saccharide moiety. In certain embodiments, the post-translational modification is made in vivo in a eukaryotic cell or in a non-eukaryotic cell.

Table 1 includes a listing of novel, humanized variable heavy, variable light, and variable heavy with variable light chain sequences of the anti-CD3 antibodies of the present invention.

TABLE 1

| SEQ ID NO: VH/VL/both | Amino Acid Sequence |
|---|---|
| 1 VH | Evqlvesggglvqpggslrlscaasgftfntyamnwvrqapgkglewvgrirskynnyatyyadsvkdrftis rddsknslylqmnslktedtavyycvrhgnfgnsyvswfaywgqgtlvtvss |
| 2 VH | evqlvesggglvqpggslrlscaasgftfntyamnwvrqapgkglewvarirskynnyatyyadsvkdrftisr ddsknslylqmnslktedtavyycvrhgnfgnsyvswfaywgqgtlvtvss |
| 3 VH | evqlvesggglvqpggslrlscaasgftfntyamnwvrqapgkglewvarirskynnyatyyadsvkdrftisr ddsknilylqmnslktedtavyycvrhgnfgnsyvswfaywgqgtlvtvss |
| 4 VL | qavvtqepsltvspggtvtltcrsstgavttsnyanwfqqkpgqaprtliygtnkrapwtparfsgsllggkaaltl sgaqpedeaeyycalwysnlwvfgggtkltvlg |
| 5 VL | qavvtqepsltvspggtvtltcrsstgavttsnyanwvqqkpgqaprgliggtnkrapgvparfsgsllggkaalt lsgaqpedeaeyycalwysnlwvfgggtkltvlg |
| 6 VL | qavvtqepsltvspggtvtltcrsstgavttsnyanwvqqkpgqaprgliggtnkrapgtparfsgsllggkaaltl sgaqpedeaeyycalwysnlwvfgggtkltvlg |
| 7 | Evqlvesggglvqpggslrlscaasgftfntyamnwvrqapgkglewvgrirskynnyatyyadsvkdrftis rddsknslylqmnslktedtavyycvrhgnfgnsyvswfaywgqgtlvtvss qavvtqepsltvspggtvtltcrsstgavttsnyanwfqqkpgqaprtliygtnkrapwtparfsgsllggkaaltl sgaqpedeaeyycalwysnlwvfgggtkltvlg |
| 8 | Evqlvesggglvqpggslrlscaasgftfntyamnwvrqapgkglewvgrirskynnyatyyadsvkdrftis rddsknslylqmnslktedtavyycvrhgnfgnsyvswfaywgqgtlvtvss qavvtqepsltvspggtvtltcrsstgavttsnyanwvqqkpgqaprgliggtnkrapgvparfsgsllggkaalt lsgaqpedeaeyycalwysnlwvfgggtkltvlg |
| 9 | Evqlvesggglvqpggslrlscaasgftfntyamnwvrqapgkglewvgrirskynnyatyyadsvkdrftis rddsknslylqmnslktedtavyycvrhgnfgnsyvswfaywgqgtlvtvss qavvtqepsltvspggtvtltcrsstgavttsnyanwvqqkpgqaprgliggtnkrapgtparfsgsllggkaaltl sgaqpedeaeyycalwysnlwvfgggtkltvlg |
| 10 | evqlvesggglvqpggslrlscaasgftfntyamnwvrqapgkglewvarirskynnyatyyadsvkdrftisr ddsknslylqmnslktedtavyycvrhgnfgnsyvswfaywgqgtlvtvss qavvtqepsltvspggtvtltcrsstgavttsnyanwfqqkpgqaprtliygtnkrapwtparfsgsllggkaaltl sgaqpedeaeyycalwysnlwvfgggtkltvlg |
| 11 | evqlvesggglvqpggslrlscaasgftfntyamnwvrqapgkglewvarirskynnyatyyadsvkdrftisr ddsknslylqmnslktedtavyycvrhgnfgnsyvswfaywgqgtlvtvss qavvtqepsltvspggtvtltcrsstgavttsnyanwvqqkpgqaprgliggtnkrapgvparfsgsllggkaalt lsgaqpedeaeyycalwysnlwvfgggtkltvlg |
| 12 | evqlvesggglvqpggslrlscaasgftfntyamnwvrqapgkglewvarirskynnyatyyadsvkdrftisr ddsknslylqmnslktedtavyyvcrhgnfgnsyvswfaywgqgtlvtvss qavvtqepsltvspggtvtltcrsstgavttsnyanwvqqkpgqaprgliggtnkrapgtparfsgsllggkaaltl sgaqpedeaeyycalwysnlwvfgggtkltvlg |
| 13 | evqlvesggglvqpggslrlscaasgftfntyamnwvrqapgkglewvarirskynnyatyyadsvkdrftisr ddsknilylqmnslktedtavyycvrhgnfgnsyvswfaywgqgtlvtvss qavvtqepsltvspggtvtltcrsstgavttsnyanwfqqkpgqaprtliygtnkrapwtparfsgsllggkaaltl sgaqpedeacyycalwysnlwvfgggtkltvlg |
| 14 | evqlvesggglvqpggslrlscaasgftfntyamnwvrqapgkglewvarirskynnyatyyadsvkdrftisr ddsknilylqmnslktedtavyycvrhgnfgnsyvswfaywgqgtlvtvss qavvtqepsltvspggtvtltcrsstgavttsnyanwvqqkpgqaprgliggtnkrapgvparfsgsllggkaalt lsgaqpedeacyycalwysnlwvfgggtkltvlg |
| 15 | evqlvesggglvqpggslrlscaasgftfntyamnwvrqapgkglewvarirskynnyatyyadsvkdrftisr ddsknilylqmnslktedtavyycvrhgnfgnsyvswfaywgqgtlvtvss qavvtqepsltvspggtvtltcrsstgavttsnyanwvqqkpgqaprgliggtnkrapgtparfsgsllggkaaltl sgaqpedeaeyycalwysnlwvfgggtkltvlg |

The antigen-binding polypeptide and the small molecule may be joined by a linker, polymer or covalent bond. The linker, polymer, or small molecule itself may comprise a functional group that is unreactive toward the 20 common amino acids. The linker or polymer may be bifunctional. One or more bonds involved in joining the antigen-binding polypeptide via the linker, polymer, or covalent bond to the biologically active molecule may be irreversible, reversible or labile under desired conditions. One or more bonds involved in joining the antigen-binding polypeptide via the linker, polymer, or covalent bond to a molecule may allow modulated release of the antigen-binding polypeptide or other molecule. A diversity of small molecules may be generated by one skilled in the art by chemical means, isolation as natural products, or other means.

Rader et al. in Proc Natl Acad Sci U.S.A. 2003 Apr. 29; 100(9):5396-400, which is incorporated by reference herein, describe a method to provide effector function and extended serum half-life to small synthetic molecules via reacting them with a generic antibody molecule. The complex described was created by a reversible covalent bond between mAb 38C2, a catalytic antibody that mimics natural aldolase enzymes, and a diketone derivative of an integrin targeting Arg-Gly-Asp peptidomimetic via a reactive lysine residue on the antibody. In addition to an increase in half life of the peptidomimetic, the complex showed selective retargeting of the antibody to the surface of integrin $\alpha_v\beta_3$ and $\alpha_v\beta_5$ expressing cells.

The present invention provides methods and compositions based on antigen-binding polypeptides, or anti-CD3 antibody, comprising at least one non-naturally encoded amino acid. Introduction of at least one non-naturally encoded amino acid into a anti-CD3 antibody can allow for the application of conjugation chemistries that involve specific chemical reactions, including, but not limited to, with one or more non-naturally encoded amino acids while not reacting with the commonly occurring 20 amino acids. In some embodiments, the anti-CD3 antibody comprising the non-naturally encoded amino acid is linked to a water soluble polymer, such as polyethylene glycol (PEG), via the side chain of the non-naturally encoded amino acid. This invention provides a highly efficient method for the selective modification of proteins with PEG derivatives, which involves the selective incorporation of non-genetically encoded amino acids, including but not limited to, those amino acids containing functional groups or substituents not found in the 20 naturally incorporated amino acids, including but not limited to a ketone, an azide or acetylene moiety, into proteins in response to a selector codon and the subsequent modification of those amino acids with a suitably reactive PEG derivative. Once incorporated, the amino acid side chains can then be modified by utilizing chemistry methodologies known to those of ordinary skill in the art to be suitable for the particular functional groups or substituents present in the naturally encoded amino acid. Known chemistry methodologies of a wide variety are suitable for use in the present invention to incorporate a water soluble polymer into the protein. Such methodologies include but are not limited to a Huisgen [3+2] cycloaddition reaction (see, e.g., Padwa, A. in *Comprehensive Organic Synthesis*, Vol. 4, (1991) Ed. Trost, B. M., Pergamon, Oxford, p. 1069-1109; and, Huisgen, R. in 1,3-*Dipolar Cycloaddition Chemistry*, (1984) Ed, Padwa, A., Wiley, New York, p. 1-176) with, including but not limited to, acetylene or azide derivatives, respectively.

Because the Huisgen [3+2] cycloaddition method involves a cycloaddition rather than a nucleophilic substitution reaction, proteins can be modified with extremely high selectivity. The reaction can be carried out at room temperature in aqueous conditions with excellent regioselectivity (1,4>1,5) by the addition of catalytic amounts of Cu(I) salts to the reaction mixture, See, e.g., Tornoe, et al., (2002) *Org. Chem.* 67:3057-3064; and, Rostovtsev, et al., (2002) *Angew. Chem. Int. Ed.* 41:2596-2599; and WO 03/101972. A molecule that can be added to a protein of the invention through a [3+2] cycloaddition includes virtually any molecule with a suitable functional group or substituent including but not limited to an azido or acetylene derivative. These molecules can be added to an unnatural amino acid with an acetylene group, including but not limited to, p-propargyloxyphenylalanine, or azido group, including but not limited to p-azido-phenylalanine, respectively.

The five-membered ring that results from the Huisgen [3+2] cycloaddition is not generally reversible in reducing environments and is stable against hydrolysis for extended periods in aqueous environments. Consequently, the physical and chemical characteristics of a wide variety of substances can be modified under demanding aqueous conditions with the active PEG derivatives of the present invention. Even more important, because the azide and acetylene moieties are specific for one another (and do not, for example, react with any of the 20 common, genetically-encoded amino acids), proteins can be modified in one or more specific sites with extremely high selectivity.

The invention also provides water soluble and hydrolytically stable derivatives of PEG derivatives and related hydrophilic polymers having one or more acetylene or azide moieties. The PEG polymer derivatives that contain acetylene moieties are highly selective for coupling with azide moieties that have been introduced selectively into proteins in response to a selector codon. Similarly, PEG polymer derivatives that contain azide moieties are highly selective for coupling with acetylene moieties that have been introduced selectively into proteins in response to a selector codon.

More specifically, the azide moieties comprise, but are not limited to, alkyl azides, aryl azides and derivatives of these azides. The derivatives of the alkyl and aryl azides can include other substituents so long as the acetylene-specific reactivity is maintained. The acetylene moieties comprise alkyl and aryl acetylenes and derivatives of each. The derivatives of the alkyl and aryl acetylenes can include other substituents so long as the azide-specific reactivity is maintained.

An anti-CD3 antibody therefore is intended to include any polypeptide that demonstrates an ability to specifically bind to a target molecule or antigen. Any known antibody or antibody fragment is an anti-CD3 antibody.

The anti-CD3 antibodies of the invention may comprise an Fc region or Fc-like region. The Fc domain provides the link to effector functions such as complement or phagocytic cells. The Fc portion of an immunoglobulin has a long plasma half-life, whereas the Fab is short-lived (Capon, et al. (1989), Nature, 337:525-531). When constructed together with a therapeutic protein, an Fc domain can provide longer half-life or incorporate such functions as Fc receptor binding, protein A binding, complement fixation and perhaps even placental transfer. For example, the Fc region of an IgG1 antibody has been fused to the N-terminal end of CD30-L, a molecule which binds CD30 receptors expressed on Hodgkin's Disease tumor cells, anaplastic lymphoma cells, T-cell leukemia cells and other malignant cell types (U.S. Pat. No. 5,480,981). IL-10, an anti-inflammatory and antirejection agent has been fused to murine Fcγ2a in order to increase the cytokine's short circulating half-life. Zheng, X. et al. (1995), The Journal of Immunology, 154: 5590-5600. Studies have also evaluated the use of tumor necrosis factor receptor linked with the Fc protein of human IgG1 to treat patients with septic shock. Fisher, C. et al., N. Engl. J. Med., 334: 1697-1702 (1996); Van Zee, K. et al., The Journal of Immunology, 156: 2221-2230 (1996) and rheumatoid arthritis (Moreland, et al. (1997), N. Engl. J. Med., 337(3):141-147. Fc has also been fused with CD4 receptor to produce a therapeutic protein for treatment of AIDS (Capon et al. (1989), Nature, 337:525-531). In addition, the N-terminus of interleukin 2 has also been fused to the Fc portion of IgG1 or IgG3 to overcome the short half life of interleukin 2 and its systemic toxicity (Harvill et al. (1995), Immunotechnology, 1: 95-105).

It is well known that Fc regions of antibodies are made up of monomeric polypeptide segments that may be linked into dimeric or multimeric forms by disulfide bonds or by non-covalent association. The number of intermolecular disulfide bonds between monomeric subunits of native Fc molecules ranges from 1 to 4 depending on the class (e.g., IgG, IgA, IgE) or subclass (e.g., IgG1, IgG2, IgG3, IgA1, IgGA2) of antibody involved. The term "Fc" as used herein is generic to the monomeric, dimeric, and multimeric forms of Fc molecules. It should be noted that Fc monomers will spontaneously dimerize when the appropriate Cys residues are present unless particular conditions are present that prevent dimerization through disulfide bond formation. Even if the Cys residues that normally form disulfide bonds in the Fc dimer are removed or replaced by other residues, the monomeric chains will generally dimerize through non-covalent interactions. The term "Fc" herein is used to mean any of these forms: the native monomer, the native dimer (disulfide bond linked), modified dimers (disulfide and/or non-covalently linked), and modified monomers (i.e., derivatives).

Variants, analogs or derivatives of the Fc portion may be constructed by, for example, making various substitutions of residues or sequences including non-naturally encoded amino acids. Variant (or analog) polypeptides include insertion variants, wherein one or more amino acid residues supplement an Fc amino acid sequence. Insertions may be located at either or both termini of the protein, or may be positioned within internal regions of the Fc amino acid sequence. Insertional variants with additional residues at either or both termini can include for example, fusion proteins and proteins including amino acid tags or labels. For example, the Fc molecule may optionally contain an N-terminal Met, especially when the molecule is expressed recombinantly in a bacterial cell such as E. coli. In Fc deletion variants, one or more amino acid residues in an Fc polypeptide are removed. Deletions can be effected at one or both termini of the Fc polypeptide, or with removal of one or more residues within the Fc amino acid sequence. Deletion variants, therefore, include all fragments of an Fc polypeptide sequence. In Fc substitution variants, one or more amino acid residues of an Fc polypeptide are removed and replaced with alternative residues. In one aspect, the substitutions are conservative in nature, however, the invention embraces substitutions that are also non-conservative. For example, cysteine residues can be deleted or replaced with other amino acids to prevent formation of some or all disulfide crosslinks of the Fc sequences. A protein may have one or more cysteine residues, and one may remove each of these cysteine residues or substitute one or more such cysteine residues with other amino acids, such as Ala or Ser, or a non-naturally encoded amino acid. As another example, modifications may also be made to introduce amino acid substitutions to (1) ablate the Fc receptor binding site; (2) ablate the complement (Clq) binding site; and/or to (3) ablate the antibody dependent cell-mediated cytotoxicity (ADCC) site. Such sites are known in the art, and any known substitutions are within the scope of Fc as used herein. For example, see Molecular Immunology, Vol. 29, No. 5, 633-639 (1992) with regards to ADCC sites in IgG1. Likewise, one or more tyrosine residues can be replaced by phenylalanine residues as well. In addition, other variant amino acid insertions, deletions (e.g., from 1-25 amino acids) and/or substitutions are also contemplated and are within the scope of the present invention. Conservative amino acid substitutions will generally be preferred. Furthermore, alterations may be in the form of altered amino acids, such as peptidomimetics or D-amino acids.

Fc sequences may also be derivatized, i.e., bearing modifications other than insertion, deletion, or substitution of amino acid residues. Preferably, the modifications are covalent in nature, and include for example, chemical bonding with polymers, lipids, other organic moieties, and inorganic moieties. Derivatives of the invention may be prepared to increase circulating half-life, or may be designed to improve targeting capacity for the polypeptide to desired cells, tissues, or organs. It is also possible to use the salvage receptor binding domain of the intact Fc molecule as the Fc part of the inventive compounds, such as described in WO 96/32478, entitled "Altered Polypeptides with Increased Half-Life". Additional members of the class of molecules designated as Fc herein are those that are described in WO 97/34631, entitled "Immunoglobulin-Like Domains with Increased Half-Lives". Both of the published PCT applications cited in this paragraph are hereby incorporated by reference.

In one embodiment, compositions of anti-CD3 antibody that include an unnatural amino acid (such as p-(propargyloxy)-phenylalanine) are provided. Various compositions comprising p-(propargyloxy)-phenylalanine and, including but not limited to, proteins and/or cells, are also provided. In one aspect, a composition that includes the p-(propargyloxy)-phenylalanine unnatural amino acid, further includes an orthogonal tRNA. The unnatural amino acid can be bonded (including but not limited to, covalently) to the orthogonal tRNA, including but not limited to, covalently bonded to the orthogonal tRNA though an amino-acyl bond, covalently bonded to a 3'OH or a 2'OH of a terminal ribose sugar of the orthogonal tRNA, etc. Cresylate, alkene, and ketone.

Measurement of Anti-CD3 Antibody Activity and Affinity of Anti-CD3 Antibody for the Anti-CD3 Antibody Antigen or Binding Partner anti-CD3 antibody activity can be determined using standard in vitro or in vivo assays. For example, cells or cell lines that bind anti-CD3 antibody (including but not limited to, cells containing native anti-CD3 antibody antigen or binding partner or recombinant anti-CD3 antibody antigen or binding partner producing cells) can be used to monitor anti-CD3 antibody binding. For a non-PEGylated or PEGylated antigen-binding polypeptide comprising a non-natural amino acid, the affinity of the anti-CD3 antibody for its antigen or binding partner can be measured by using techniques known in the art such as a BIAcore™ biosensor (Pharmacia).

Regardless of which methods are used to create the anti-CD3 antibody's, the anti-CD3 antibody's are subject to assays for biological activity. Tritiated thymidine assays may be conducted to ascertain the degree of cell division, if appropriate. Other biological assays, however, may be used to ascertain the desired activity. Biological assays such as measuring the ability to inhibit an antigen's biological activity, such as an enzymatic, proliferative, or metabolic activity also provides an indication of anti-CD3 antibody activity. Other in vitro assays may be used to ascertain biological activity. In general, the test for biological activity should provide analysis for the desired result, such as increase or decrease in biological activity (as compared to non-altered anti-CD3 antibody), different biological activity (as compared to non-altered anti-CD3 antibody), receptor affinity analysis, conformational or structural changes, or serum half-life analysis, as appropriate for the antigen's biological activity.

The above compilation of references for assay methodologies is not exhaustive, and those skilled in the art will recognize other assays useful for testing for the desired end result.

Measurement of Potency, Functional In Vivo Half-Life, and Pharmacokinetic Parameters An important aspect of the invention is the prolonged biological half-life that is obtained by construction of anti- CD3 antibody with or without conjugation of the anti-CD3 antibody to a water soluble polymer moiety. The rapid decrease of anti-CD3 antibody serum concentrations has made it important to evaluate biological responses to treatment with conjugated and non-conjugated anti-CD3 antibody and variants thereof. Preferably, the conjugated and non-conjugated anti-CD3 antibody and variants thereof of the present invention have prolonged serum half-lives also after i.v. administration, making it possible to measure by, e.g. ELISA method or by a primary screening assay. Measurement of in vivo biological half-life is carried out as described herein.

Pharmacokinetic parameters for an antigen-binding polypeptide comprising a non-naturally encoded amino acid can be evaluated in normal Sprague-Dawley male rats (N=5 animals per treatment group). Animals will receive either a single dose of 25 ug/rat iv or 50 ug/rat sc, and approximately 5-7 blood samples will be taken according to a pre-defined time course, generally covering about 6 hours for an antigen-binding polypeptide comprising a non-naturally encoded amino acid not conjugated to a water soluble polymer and about 4 days for an antigen-binding polypeptide comprising a non-naturally encoded amino acid and conjugated to a water soluble polymer. Pharmacokinetic data for anti-CD3 antibody is well-studied in several species and can be compared directly to the data obtained for anti-CD3 antibody comprising a non-naturally encoded amino acid.

The specific activity of anti-CD3 antibody in accordance with this invention can be determined by various assays known in the art. The biological activity of the anti-CD3 antibody muteins, or fragments thereof, obtained and purified in accordance with this invention can be tested by methods described or referenced herein or known to those skilled in the art.

Administration and Pharmaceutical Compositions

The polypeptides or proteins of the invention (including but not limited to, anti-CD3 antibody, synthetases, proteins comprising one or more unnatural amino acid, etc.) are optionally employed for therapeutic uses, including but not limited to, in combination with a suitable pharmaceutical carrier. Such compositions, for example, comprise a therapeutically effective amount of the compound, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering proteins are well known in the art and can be applied to administration of the polypeptides of the invention.

Therapeutic compositions comprising one or more polypeptide of the invention are optionally tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of unnatural herein to natural amino acid homologues (including but not limited to, comparison of a anti-CD3 antibody modified to include one or more unnatural amino acids to a natural amino acid anti-CD3 antibody), i.e., in a relevant assay.

Administration is by any of the routes normally used for introducing a molecule into ultimate contact with blood or tissue cells. The unnatural amino acid polypeptides of the invention are administered in any suitable manner, optionally with one or more pharmaceutically acceptable carriers. Suitable methods of administering such polypeptides in the context of the present invention to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Polypeptide compositions can be administered by a number of routes including, but not limited to oral, intravenous, intraperitoneal, intramuscular, transdermal, subcutaneous, topical, sublingual, or rectal means. Compositions comprising non-natural amino acid polypeptides, modified or unmodified, can also be administered via liposomes. Such administration routes and appropriate formulations are generally known to those of skill in the art.

The anti-CD3 antibody comprising a non-natural amino acid, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged anti-CD3 antibody can be presented in unit-dose or multi-dose sealed containers, such as ampules and vials.

Parenteral administration and intravenous administration are preferred methods of administration. In particular, the routes of administration already in use for natural amino acid homologue therapeutics (including but not limited to, those typically used for EPO, GH, anti-CD3 antibody, G-CSF, GM-CSF, IFNs, interleukins, antibodies, and/or any other pharmaceutically delivered protein), along with formulations in current use, provide preferred routes of administration and formulation for the polypeptides of the invention.

The dose administered to a patient, in the context of the present invention, is sufficient to have a beneficial therapeutic response in the patient over time, or, including but not limited to, to inhibit infection by a pathogen, or other appropriate activity, depending on the application. The dose is determined by the efficacy of the particular vector, or formulation, and the activity, stability or serum half-life of the unnatural amino acid polypeptide employed and the condition of the patient, as well as the body weight or surface area of the patient to be treated. The size of the dose is also determined by the existence, nature, and extent of any adverse side-effects that accompany the administration of a particular vector, formulation, or the like in a particular patient.

In determining the effective amount of the vector or formulation to be administered in the treatment or prophylaxis of disease (including but not limited to, cancers, inherited diseases, diabetes, AIDS, or the like), the physician evaluates circulating plasma levels, formulation toxicities, progression of the disease, and/or where relevant, the production of anti-unnatural amino acid polypeptide antibodies.

The dose administered, for example, to a 70 kilogram patient, is typically in the range equivalent to dosages of currently-used therapeutic proteins, adjusted for the altered activity or serum half-life of the relevant composition. The vectors of this invention can supplement treatment conditions by any known conventional therapy, including antibody administration, vaccine administration, administration of cytotoxic agents, natural amino acid polypeptides, nucleic acids, nucleotide analogues, biologic response modifiers, and the like.

For administration, formulations of the present invention are administered at a rate determined by the LD-50 or ED-50 of the relevant formulation, and/or observation of any side-effects of the unnatural amino acids at various concentrations, including but not limited to, as applied to the mass and overall health of the patient. Administration can be accomplished via single or divided doses.

If a patient undergoing infusion of a formulation develops fevers, chills, or muscle aches, he/she receives the appropriate dose of aspirin, ibuprofen, acetaminophen or other pain/fever controlling drug. Patients who experience reactions to the infusion such as fever, muscle aches, and chills are premedicated 30 minutes prior to the future infusions with either aspirin, acetaminophen, or, including but not limited to, diphenhydramine. Meperidine is used for more severe chills and muscle aches that do not quickly respond to antipyretics and antihistamines. Cell infusion is slowed or discontinued depending upon the severity of the reaction.

Human antigen-binding polypeptides of the invention can be administered directly to a mammalian subject. Administration is by any of the routes normally used for introducing anti-CD3 antibody to a subject. The anti-CD3 antibody compositions according to embodiments of the present invention include those suitable for oral, rectal, topical, inhalation (including but not limited to, via an aerosol), buccal (including but not limited to, sub-lingual), vaginal, parenteral (including but not limited to, subcutaneous, intramuscular, intradermal, intraarticular, intrapleural, intraperitoneal, inracerebral, intraarterial, or intravenous), topical (i.e., both skin and mucosal surfaces, including airway surfaces) and transdermal administration, although the most suitable route in any given case will depend on the nature and severity of the condition being treated. Administration can be either local or systemic. The formulations of compounds can be presented in unit-dose or multi-dose sealed containers, such as ampoules and vials. Anti-CD3 antibody of the invention can be prepared in a mixture in a unit dosage injectable form (including but not limited to, solution, suspension, or emulsion) with a pharmaceutically acceptable carrier. Anti-CD3 antibody of the invention can also be administered by continuous infusion (using, including but not limited to, minipumps such as osmotic pumps), single bolus or slow-release depot formulations.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. Solutions and suspensions can be prepared from sterile powders, granules, and tablets of the kind previously described.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions (including optional pharmaceutically acceptable carriers, excipients, or stabilizers) of the present invention (see, e.g., Remington's Pharmaceutical Sciences, 17$^{th}$ ed. 1985)).

Suitable carriers include buffers containing phosphate, borate, HEPES, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates, including glucose, mannose, or dextrins; chelating agents such as EDTA; divalent metal ions such as zinc, cobalt, or copper; sugar alcohols such as mannitol or sorbitol; salt-forming counter ions such as sodium; and/or nonionic surfactants such as Tween™, Pluronics™, or PEG.

The anti-CD3 antibodies of the invention, including those linked to water soluble polymers such as PEG can also be administered by or as part of sustained-release systems. Sustained-release compositions include, including but not limited to, semi-permeable polymer matrices in the form of shaped articles, including but not limited to, films, or microcapsules. Sustained-release matrices include from biocompatible materials such as poly(2-hydroxyethyl methacrylate) (Langer et al., *J. Biomed. Mater, Res.,* 15: 167-277 (1981); Langer, *Chem. Tech.,* 12: 98-105 (1982), ethylene vinyl acetate (Langer et at, supra) or poly-D-(-)-3-hydroxybutyric acid (EP 133,988), polylactides (polylactic acid) (U.S. Pat. No. 3,773,919; EP 58,481), polyglycolide (polymer of glycolic acid), polylactide co-glycolide (copolymers of lactic acid and glycolic acid) polyanhydrides, copolymers of L-glutamic acid and gamma-ethyl-L-glutamate (U. Sidman et al., *Biopolymers,* 22, 547-556 (1983), poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Sustained-release compositions also include a liposomally entrapped compound. Liposomes containing the compound are prepared by methods known per se: DE 3,218,121; Epstein et al., *Proc. Natl. Acad. Sci, U.S.A.,* 82: 3688-3692 (1985); Hwang et al., *Proc. Natl. Acad. Sci. U.S.A.,* 77: 4030-4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. All references and patents cited are incorporated by reference herein.

Liposomally entrapped anti-CD3 antibody can be prepared by methods described in, e.g., DE 3,218,121; Epstein et al., *Proc. Natl. Acad. Sci. U.S.A.,* 82: 3688-3692 (1985); Hwang et al., *Proc. Natl, Acad. Sci. USA.,* 77: 4030-4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. Composition and size of liposomes are well known or able to be readily determined empirically by one skilled in the art. Some examples of liposomes as described in, e.g., Park J W, et al., *Proc. Natl. Acad. Sci. USA* 92:1327-1331 (1995); Lasic D and Papahadjopoulos D (eds): MEDICAL APPLICATIONS OF LIPOSOMES (1998); Drummond D C, et al., Liposomal drug delivery systems for cancer therapy, in Teicher B (ed): CANCER DRUG DISCOVERY AND DEVELOPMENT (2002); Park J W, et al., *Clin. Cancer Res.* 8:1172-1181 (2002); Nielsen U B, et al., *Biochim. Biophys. Acta* 1591(1-3):109-118 (2002); Mamot C, et al., *Cancer Res.* 63: 3154-3161 (2003). All references and patents cited are incorporated by reference herein.

The dose administered to a patient in the context of the present invention should be sufficient to cause a beneficial response in the subject over time. Generally, the total pharmaceutically effective amount of the anti-CD3 antibody of the present invention administered parenterally per dose is in the range of about 0.01 ug/kg/day to about 100 μg/kg, or about 0.05 mg/kg to about 1 mg/kg, of patient body weight, although this is subject to therapeutic discretion. The frequency of dosing is also subject to therapeutic discretion, and may be more frequent or less frequent than the commercially available anti-CD3 antibody products approved for use in humans. Generally, a PEGylated antigen-binding polypeptide of the invention can be administered by any of the routes of administration described above.

Therapeutic Uses of Antigen-Binding Polypeptides of the Invention

The anti-CD3 antibody polypeptides of the invention are useful for treating a wide range of disorders. The pharmaceutical compositions containing the anti-CD3 antibody may be formulated at a strength effective for administration by various means to a human patient experiencing disorders that may be affected by anti-CD3 antibody agonists or antagonists, such as but not limited to, anti-proliferatives, anti-inflammatory, or anti-virals are used, either alone or as part of a condition or disease. Average quantities of anti-CD3 antibody may vary and in particular should be based upon the recommendations and prescription of a qualified physician. The exact amount of anti-CD3 antibody is a matter of preference subject to such factors as the exact type of condition being treated, the condition of the patient being treated, as well as the other ingredients in the composition. The invention also provides for administration of a therapeutically effective amount of another active agent such as an anti-cancer chemotherapeutic agent. The amount to be given may be readily determined by one skilled in the art based upon therapy with anti-CD3 antibody.

EXAMPLES

The following examples are offered to illustrate, but not to limit the claimed invention.

Example 1

This example describes one of the many potential sets of criteria for the selection of preferred sites of incorporation of non-naturally encoded amino acids into anti-CD3 antibody.

This example demonstrates how preferred sites within the antigen-binding polypeptide were selected for introduction of a non-naturally encoded amino acid. The three dimensional structure composed of two molecules of anti-CD3 antibody, or the secondary, tertiary, or quaternary structure of anti-CD3 antibody was used to determine preferred positions into which one or more non-naturally encoded amino acids could be introduced.

The following criteria were used to evaluate each position of anti-CD3 antibody for the introduction of a non-naturally encoded amino acid: the residue (a) should not interfere with binding of either anti-CD3 antibody based on structural analysis of three dimensional structures, or the secondary, tertiary, or quaternary structure of anti-CD3 antibody, b) should not be affected by alanine or homolog scanning mutagenesis (c) should be surface exposed and exhibit minimal van der Waals or hydrogen bonding interactions with surrounding residues, (d) may be on one or more of the exposed faces of anti-CD3 antibody, (e) may be a site or sites of anti-CD3 antibody that are juxtaposed to a second anti-CD3 antibody, or other molecule or fragment thereof, (f) should be either deleted or variable in anti-CD3 antibody variants, (g) would result in conservative changes upon substitution with a non-naturally encoded amino acid, (h) may modulate the conformation of the anti-CD3 antibody itself or a dimer or multimer comprising one or more anti-CD3 antibody, by altering the flexibility or rigidity of the complete structure as desired, (i) could be found in either highly flexible regions or structurally rigid regions and (j) are found in complementarity determining regions (CDR) or not. In addition, further calculations were performed on the anti-CD3 antibody molecule, utilizing the Cx program (Pintar et al. *Bioinformatics,* 18, pp 980) to evaluate the extent of protrusion for each protein atom. As a result, in some embodiments, the non-naturally encoded encoded amino acid is substituted at, but not limited to, one or more positions of anti-CD3 antibody.

Example 2

This example details cloning and expression of anti-CD3 antibody including a non-naturally encoded amino acid in *E. coli.*

An introduced translation system that comprises an orthogonal tRNA (O-tRNA) and an orthogonal aminoacyl tRNA synthetase (O-RS) is used to express anti-CD3 antibody containing a non-naturally encoded amino acid. The O-RS preferentially aminoacylates the O-tRNA with a non-naturally encoded amino acid. In turn the translation system inserts the non-naturally encoded amino acid into anti-CD3 antibody, in response to an encoded selector codon.

The transformation of *E. coli* with plasmids containing the modified anti-CD3 antibody gene and the orthogonal aminoacyl tRNA synthetase/tRNA pair (specific for the desired non-naturally encoded amino acid) allows the site-specific incorporation of non-naturally encoded amino acid into the anti-CD3 antibody. The transformed *E. coli*, grown at 37° C. in media containing between 0.01-100 mM of the particular non-naturally encoded amino acid, expresses modified anti-CD3 antibody with high fidelity and efficiency. The His-tagged anti-CD3 antibody containing a non-naturally encoded amino acid is produced by the *E. coli* host cells as inclusion bodies or aggregates. The aggregates are solubilized and affinity purified under denaturing conditions in 6M guanidine HCl. Refolding is performed by dialysis at 4° C. overnight in 50 mM TRIS-HCl, pH8.0, 40 μM $CuSO_4$, and 2% (w/v) Sarkosyl. The material is then dialyzed against 20 mM TRIS-HCl, pH 8.0, 100 mM NaCl, 2 mM $CaCl_2$, followed by removal of the His-tag. See Boissel et al., (1993) 268:15983-93. Methods for purification of anti-CD3 antibody are well known in the art and are confirmed by SDS-PAGE, Western Blot analyses, or electrospray-ionization ion trap mass spectrometry and the like.

Expression/Suppression

Suppression with para-acetyl-phenylalanine (pAcF): Suppression of the amber mutations in *E. coli* was achieved using standard protocols known in the art. Briefly, for the periplasmic suppression of antibody fragments in *E. coli* (scFv and Fab), the expression vector construct was transformed into *E. coli* host cells with a plasmid encoding the orthogonal tyrosyl-tRNA-synthetase from M. jannaschii (MjTyrRS). Overnight bacterial cultures were diluted 1:100 into shake flasks containing either LB media (Luria-Bertani) or Superbroth, and grown at 37° C. to an OD of approximately 0.8. Fab and scFv expression was induced while suppression of the amber codon was achieved by the addition of para-acetyl-phenylalanine (pAcF) to a final concentration of 4 mM. Cultures were incubated at 25° C. overnight.

Suppression with aa9.2: Suppression of amber mutations with a derivative of pAcF (aa 9.2) was achieved in a similar manner as pAcF, except that the orthogonal tyrosyl-tRNA-synthetase from *M. jannaschii* (MjTyrRS) used was specific for this amino acid. Suppression was achieved by the addition of aa9.2 (4 mM) at the time of induction.

Protein Extraction and Purification

Cells were harvested by centrifugation and resuspended in periplasmic release buffer (50 mM NaPO$_4$, 20% sucrose, 1 mM EDTA, pH 8.0) supplemented with 100 ug/ml of lysozyme and incubated on ice for 30 minutes. After centrifugation, antibody fragments in the supernatant were immobilized on ProBind beads (Invitrogen; Carlsbad, CA) by virtue of their His tag, the beads washed extensively with binding buffer and then the bound fragments eluted from the beads with 0.5 M imidazole. Purified fragments were dialyzed in storage buffer (50 mM HEPES, 150 mM NaCl, 10% glycerol, 5% sucrose, pH 7.8). For small scale analysis of scFv fragments expressed in the cytoplasm, *E. coli* from 15 ml of culture were collected by centrifugation and resuspended in 1 ml of lysis buffer (B-PER, Pierce Biotechnology; Rockford, IL) supplemented with 10 ug/ml of DNase. The mixture was incubated at 37° C. for 30 minutes, diluted to 1× in Protein Loading buffer (Invitrogen; Carlsbad, CA) and analyzed by SDS-PAGE.

Example 3

This example details introduction of a carbonyl-containing amino acid and subsequent reaction with an aminooxy-containing PEG.

This Example demonstrates a method for the generation of an antigen-binding polypeptide that incorporates a ketone-containing non-naturally encoded amino acid that is subsequently reacted with an aminooxy-containing PEG of approximately 5,000 MW. Each of the residues identified according to the criteria of Example 1 is separately substituted with a non-naturally encoded amino acid having the following structure:

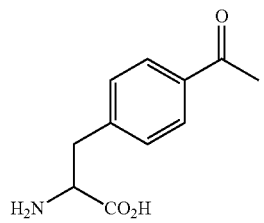

Once modified, the anti-CD3 antibody variant comprising the carbonyl-containing amino acid is reacted with an aminooxy-containing PEG derivative of the form:

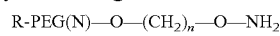

where R is methyl, n is 3 and N is approximately 5,000 MW. The purified anti-CD3 antibody containing p-acetylphenylalanine dissolved at 10 mg/mL in 25 mM MES (Sigma Chemical, St. Louis, MO) pH 6.0, 25 mM Hepes (Sigma Chemical, St. Louis, MO) pH 7.0, or in 10 mM Sodium Acetate (Sigma Chemical, St. Louis, MO) pH 4.5, is reacted with a 10 to 100-fold excess of aminooxy-containing PEG, and then stirred for 10-16 hours at room temperature (Jencks, W. *J. Am. Chem. Soc.* 1959, 81, pp 475). The PEG-anti-CD3 antibody is then diluted into appropriate buffer for immediate purification and analysis.

Example 4

Conjugation with a PEG consisting of a hydroxylamine group linked to the PEG via an amide linkage.

A PEG reagent having the following structure is coupled to a ketone-containing non-naturally encoded amino acid using the procedure described in Example 3:

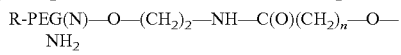

where R=methyl, n=4 and N is approximately 20,000 MW. The reaction, purification, and analysis conditions are as described in Example 3.

Example 5

This example details the introduction of two distinct non-naturally encoded amino acids into anti-CD3 antibody.

This example demonstrates a method for the generation of an antigen-binding polypeptide that incorporates non-naturally encoded amino acid comprising a ketone functionality at two positions identified according to Example 1, wherein X* represents a non-naturally encoded amino acid. The antigen-binding polypeptide is prepared as described in Examples 1 and 2, except that the suppressor codon is introduced at two distinct sites within the nucleic acid.

Example 6

This example details conjugation of antigen-binding polypeptide to a hydrazide-containing PEG and subsequent in situ reduction.

An antigen-binding polypeptide incorporating a carbonyl-containing amino acid is prepared according to the procedure described in Examples 2 and 3. Once modified, a hydrazide-containing PEG having the following structure is conjugated to the anti-CD3 antibody:

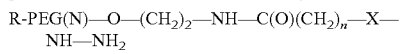

where R=methyl, n=2 and N=10,000 MW and X is a carbonyl (C=O) group. The purified anti-CD3 antibody containing p-acetylphenylalanine is dissolved at between 0.1-10 mg/mL in 25 mM MES (Sigma Chemical, St. Louis, MO) pH 6.0, 25 mM Hepes (Sigma Chemical, St. Louis, MO) pH 7.0, or in 10 mM Sodium Acetate (Sigma Chemical, St. Louis, MO) pH 4.5, is reacted with a 1 to 100-fold excess of hydrazide-containing PEG, and the corresponding hydrazone is reduced in situ by addition of stock 1M NaCNBH$_3$ (Sigma Chemical, St. Louis, MO), dissolved in H$_2$O, to a final concentration of 10-50 mM. Reactions are carried out in the dark at 4° C. to RT for 18-24 hours. Reactions are stopped by addition of 1 M Tris (Sigma Chemical, St. Louis, MO) at about pH 7.6 to a final Tris concentration of 50 mM or diluted into appropriate buffer for immediate purification.

Example 7

This example details introduction of an alkyne-containing amino acid into a anti-CD3 antibody and derivatization with mPEG-azide.

Any of the residues identified according to Example 1 are substituted with the following non-naturally encoded amino acid:

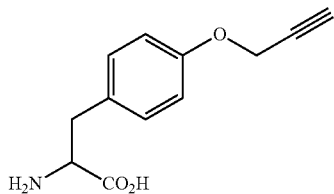 [SMILES: C#CCOc1ccc(CC(N)C(=O)O)cc1]

The purified anti-CD3 antibody containing propargyl-tyrosine dissolved at between 0.1-10 mg/mL in PB buffer (100 mM sodium phosphate, 0.15 M NaCl, pH=8) and a 10 to 1000-fold excess of an azide-containing PEG is added to the reaction mixture. A catalytic amount of $CuSO_4$ and Cu wire are then added to the reaction mixture. After the mixture is incubated (including but not limited to, about 4 hours at room temperature or 37° C., or overnight at 4° C.), $H_2O$ is added and the mixture is filtered through a dialysis membrane. The sample can be analyzed for the addition, including but not limited to, by similar procedures described in Example 3.

In this Example, the PEG will have the following structure:

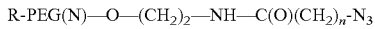

R-PEG(N)—O—$(CH_2)_2$—NH—$C(O)(CH_2)_n$-$N_3$ where A is methyl, n is 4 and N is 10,000 MW.

Example 8

This example details substitution of a large, hydrophobic amino acid in anti-CD3 antibody with propargyl tyrosine.

A Phe, Trp or Tyr residue present within the sequence of anti-CD3 antibody is substituted with the following non-naturally encoded amino acid as described in Example 7:

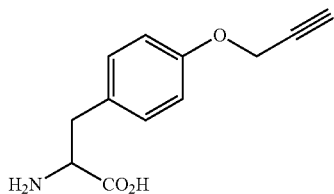 [SMILES: C#CCOc1ccc(CC(N)C(=O)O)cc1]

Once modified, a PEG is attached to the anti-CD3 antibody variant comprising the alkyne-containing amino acid. The PEG will have the following structure:

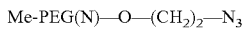

Me-PEG(N)—O—$(CH_2)_2$—$N_3$ and coupling procedures would follow those in Example 7. This will generate a anti-CD3 antibody variant comprising a non-naturally encoded amino acid that is approximately isosteric with one of the naturally-occurring, large hydrophobic amino acids and which is modified with a PEG derivative at a distinct site within the polypeptide.

Example 9

This example details generation of a anti-CD3 antibody homodimer, heterodimer, homomultimer, or heteromultimer separated by one or more PEG linkers.

The alkyne-containing anti-CD3 antibody variant produced in Example 7 is reacted with a bifunctional PEG derivative of the form:

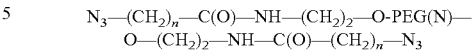

$N_3$—$(CH_2)_n$—C(O)—NH—$(CH_2)_2$—O-PEG(N)—O—$(CH_2)_2$—NH—C(O)—$(CH_2)_n$—$N_3$ where n is 4 and the PEG has an average MW of approximately 5,000, to generate the corresponding anti-CD3 antibody homodimer where the two anti-CD3 antibody molecules are physically separated by PEG. In an analogous manner an antigen-binding polypeptide may be coupled to one or more other polypeptides to form heterodimers, homomultimers, or heteromultimers. Coupling, purification, and analyses will be performed as in Examples 7 and 3.

Example 10

This example describes methods to measure in vitro and in vivo activity of anti-CD3 antibody comprising a non-naturally encoded amino acid and PEGylated anti-CD3 antibody.

Cell Binding Assays

Cells ($3 \times 10^6$) are incubated in duplicate in PBS/1% BSA (100 µl) in the absence or presence of various concentrations (volume: 10 µl) of unlabeled anti-CD3 antibody, anti-CD3 antibody or a negative control and in the presence of $^{125}$I-anti-CD3 antibody (approx. 100,000 cpm or 1 ng) at 0° C. for 90 minutes (total volume: 120 µl). Cells are then resuspended and layered over 200 µl ice cold FCS in a 350 µl plastic centrifuge tube and centrifuged (1000 g; 1 minute). The pellet is collected by cutting off the end of the tube and pellet and supernatant counted separately in a gamma counter (Packard).

Specific binding (cpm) is determined as total binding in the absence of a competitor (mean of duplicates) minus binding (cpm) in the presence of 100-fold excess of unlabeled anti-CD3 antibody (non-specific binding). The non-specific binding is measured for each of the cell types used. Experiments are run on separate days using the same preparation of $^{125}$I-anti-CD3 antibody and should display internal consistency. The binding is inhibited in a dose dependent manner by unlabeled natural anti-CD3 antibody or anti-CD3 antibody, but not by the negative control. The ability of anti-CD3 antibody to compete for the binding of natural $^{125}$I-anti-CD3 antibody suggests that the receptors recognize both forms equally well.

In Vivo Studies of PEGylated Anti-CD3 Antibody

PEG-anti-CD3 antibody, unmodified anti-CD3 antibody and buffer solution are administered to mice or rats. The results will show superior activity and prolonged half life of the PEGylated anti-CD3 antibody of the present invention compared to unmodified anti-CD3 antibody.

Measurement of the In Vivo Half-Life of Conjugated and Non-Conjugated Anti-CD3 Antibody and Variants Thereof.

Male Sprague Dawley rats (about 7 weeks old) are used. On the day of administration, the weight of each animal is measured. 100 µg per kg body weight of the non-conjugated and conjugated anti-CD3 antibody samples are each injected intravenously into the tail vein of three rats. At 1 minute, 30 minutes, 1, 2, 4, 6, and 24 hours after the injection, 500 µl of blood is withdrawn from each rat while under $CO_2$-anesthesia. The blood samples are stored at room temperature for 1.5 hours followed by isolation of serum by centrifugation (4° C., 18000×g for 5 minutes). The serum samples are stored at −80° C. until the day of analysis. The amount of active anti-CD3 antibody in the serum samples is quantified by the anti-CD3 antibody in vitro activity assay after thawing the samples on ice.

Example 11

Human Clinical Trial of the Safety and/or Efficacy of PEGylated anti-CD3 antibody Comprising a Non-Naturally Encoded Amino Acid.

Objective To compare the safety and pharmacokinetics of subcutaneously administered PEGylated recombinant huma anti-CD3 antibody comprising a non-naturally encoded amino acid with a commercially available product specific for the same target antigen (e.g. Herceptin®, Bexxar®, Campath®, CEA-Scan®, Enbrel®, Erbitux®, Humira®, Myoscint®, Prostascint®, Raptiva®, Remicade®, Reo-Pro®, Rituxan®, Simulect®, Synagis®, Verluma®, Xolair®, Zenapax®, Zevalin®, or Avastin®.

Patients Eighteen healthy volunteers ranging between 20-40 years of age and weighing between 60-90 kg are enrolled in the study. The subjects will have no clinically significant abnormal laboratory values for hematology or serum chemistry, and a negative urine toxicology screen, HIV screen, and hepatitis B surface antigen. They should not have any evidence of the following: hypertension; a history of any primary hematologic disease; history of significant hepatic, renal, cardiovascular, gastrointestinal, genitourinary, metabolic, neurologic disease; a history of anemia or seizure disorder; a known sensitivity to bacterial or mammalian-derived products, PEG, or human serum albumin; habitual and heavy consumer to beverages containing caffeine; participation in any other clinical trial or had blood transfused or donated within 30 days of study entry; had exposure to anti-CD3 antibody within three months of study entry; had an illness within seven days of study entry; and have significant abnormalities on the pre-study physical examination or the clinical laboratory evaluations within 14 days of study entry. All subjects are evaluable for safety and all blood collections for pharmacokinetic analysis are collected as scheduled. All studies are performed with institutional ethics committee approval and patient consent.

Study Design This will be a Phase I, single-center, open-label, randomized, two-period crossover study in healthy male volunteers. Eighteen subjects are randomly assigned to one of two treatment sequence groups (nine subjects/group). anti-CD3 antibody is administered over two separate dosing periods as a bolus s.c. injection in the upper thigh using equivalent doses of the PEGylated anti-CD3 antibody comprising a non-naturally encoded amino acid and the commercially available product chosen. The dose and frequency of administration of the commercially available product is as instructed in the package label. Additional dosing, dosing frequency, or other parameter as desired, using the commercially available products may be added to the study by including additional groups of subjects. Each dosing period is separated by a 14-day washout period. Subjects are confined to the study center at least 12 hours prior to and 72 hours following dosing for each of the two dosing periods, but not between dosing periods. Additional groups of subjects may be added if there are to be additional dosing, frequency, or other parameter, to be tested for the PEGylated anti-CD3 antibody as well. The experimental formulation of anti-CD3 antibody is the PEGylated anti-CD3 antibody comprising a non-naturally encoded amino acid.

Blood Sampling Serial blood is drawn by direct vein puncture before and after administration of anti-CD3 antibody. Venous blood samples (5 mL) for determination of serum anti-CD3 antibody concentrations are obtained at about 30, 20, and 10 minutes prior to dosing (3 baseline samples) and at approximately the following times after dosing: 30 minutes and at 1, 2, 5, 8, 12, 15, 18, 24, 30, 36, 48, 60 and 72 hours. Each serum sample is divided into two aliquots. All serum samples are stored at −20° C. Serum samples are shipped on dry ice. Fasting clinical laboratory tests (hematology, serum chemistry, and urinalysis) are performed immediately prior to the initial dose on day 1, the morning of day 4, immediately prior to dosing on day 16, and the morning of day 19.

Bioanalytical Methods A radioimmunoassay (RA) or ELISA kit procedure is used for the determination of serum anti-CD3 antibody concentrations.

Safety Determinations Vital signs are recorded immediately prior to each dosing (Days 1 and 16), and at 6, 24, 48, and 72 hours after each dosing. Safety determinations are based on the incidence and type of adverse events and the changes in clinical laboratory tests from baseline. In addition, changes from pre-study in vital sign measurements, including blood pressure, and physical examination results are evaluated.

Data Analysis Post-dose serum concentration values are corrected for pre-dose baseline anti-CD3 antibody concentrations by subtracting from each of the post-dose values the mean baseline anti-CD3 antibody concentration determined from averaging the anti-CD3 antibody levels from the three samples collected at 30, 20, and 10 minutes before dosing. Pre-dose serum anti-CD3 antibody concentrations are not included in the calculation of the mean value if they are below the quantification level of the assay. Pharmacokinetic parameters are determined from serum concentration data corrected for baseline anti-CD3 antibody concentrations. Pharmacokinetic parameters are calculated by model independent methods on a Digital Equipment Corporation VAX 8600 computer system using the latest version of the BIO-AVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Safety Results The incidence of adverse events is equally distributed across the treatment groups. There are no clinically significant changes from baseline or pre-study clinical laboratory tests or blood pressures, and no notable changes from pre-study in physical examination results and vital sign measurements. The safety profiles for the two treatment groups should appear similar.

Pharmacokinetic Results Mean serum anti-CD3 antibody concentration-time profiles (uncorrected for baseline anti-CD3 antibody levels) in all 18 subjects after receiving a single dose of one or more of commercially available products specific for the same target antigen are compared to the PEGylated anti-CD3 antibody comprising a non-naturally encoded amino acid at each time point measured. All subjects should have pre-dose baseline anti-CD3 antibody concentrations within the normal physiologic range. Pharmacokinetic parameters are determined from serum data corrected for pre-dose mean baseline anti-CD3 antibody concentrations and the $C_{max}$ and $t_{max}$ are determined. The mean $t_{max}$ for the clinical comparator(s) chosen is significantly shorter than the $t_{max}$ for the PEGylated anti-CD3 antibody comprising the non-naturally encoded amino acid. Terminal half-life values are significantly shorter for the commerically available anti-CD3 antibody products tested compared with the terminal half-life for the PEGylated anti-CD3 antibody comprising a non-naturally encoded amino acid.

Although the present study is conducted in healthy male subjects, similar absorption characteristics and safety profiles would be anticipated in other patient populations; such as male or female patients with cancer or chronic renal failure, pediatric renal failure patients, patients in autologous predeposit programs, or patients scheduled for elective surgery.

In conclusion, subcutaneously administered single doses of PEGylated anti-CD3 antibody comprising non-naturally encoded amino acid will be safe and well tolerated by healthy male subjects. Based on a comparative incidence of adverse events, clinical laboratory values, vital signs, and physical examination results, the safety profiles of the commercially available forms of anti-CD3 antibody and PEGylated anti-CD3 antibody comprising non-naturally encoded amino acid will be equivalent. The PEGylated anti-CD3 antibody comprising non-naturally encoded amino acid potentially provides large clinical utility to patients and health care providers.

Example 12

The affinity and specificity of the anti-CD3 Fab-folate conjugate were evaluated using $FR^+$ and $FR^-$ cell lines. After culture in folate deficient media, FR was overexpressed in nasopharyngeal (KB) and ovarian (OV-90, SKOV-3) cancer cell lines as determined by flow cytometry. A kidney cancer cell line CAKI-1 and an alveolar basal epithelial cell carcinoma A549 that did not express FR were used as negative controls. The anti-CD3 Fab-folate conjugate was able to bind to KB cells ($FR^+$) with affinity similar to free folate indicating minimal loss of binding to the folate receptor as a result of conjugation with the anti-CD3 Fab. Likewise, the anti- CD3 Fab-folate bound to Jurkat cells ($CD3^+$) with similar affinity to anti-CD3; no binding was observed to A549 cells ($FR^-$).

Example 13

Figure 2:
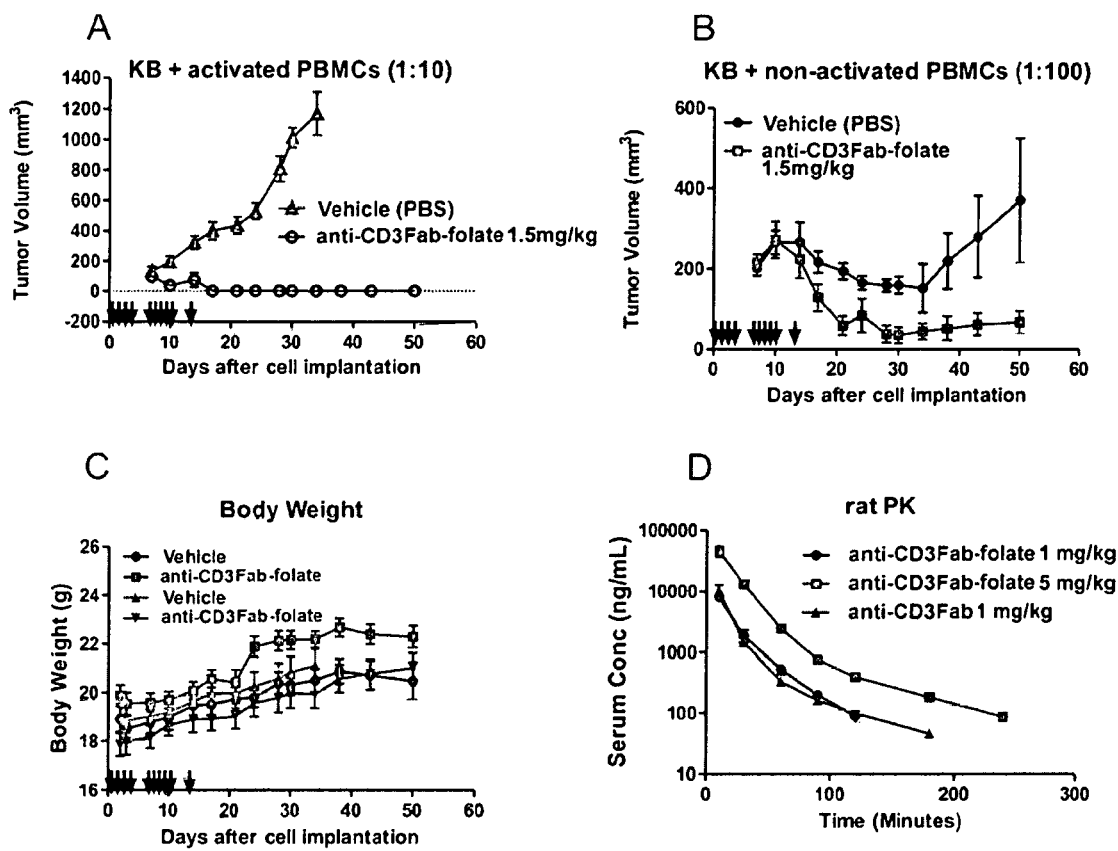
FIG. 2—The in vivo efficacy of the anti-CD3 Fab-folate bispecific agent was assessed in a xenograft model using female NOD-SCID mice. Animals were maintained on a low-folate diet to reduce circulating serum levels of folate that might compete with the bispecific agent. KB (FR+) or A549 (FR−) cells were able to form tumors when mixed with non-activated human PBMCs (ratio 1:100 of target: effector cells) or activated human PBMCs (ratio 1:10 of target: effector cells) and injected subcutaneously into mice. KB cells mixed with activated human PBMCs (ratio 1:10 of target: effector cells) were implanted into mice and then the mice were injected intravenously with 1.5 mg/kg of anti-CD3 Fab-folate or PBS daily for 10 days starting on the same day as tumor cell implantation.
Figure 4:
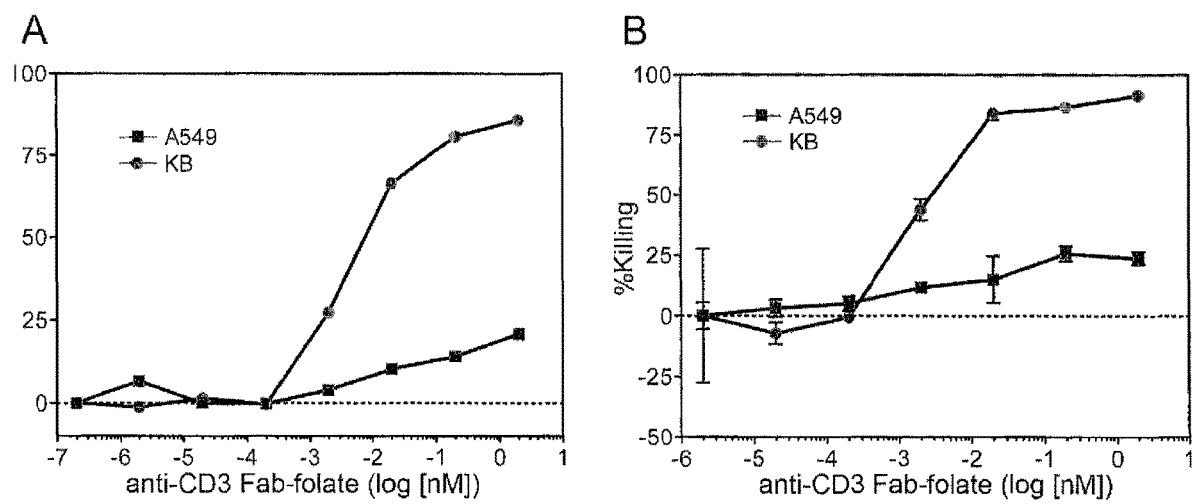
FIG. 4—Shows the T cell mediated toxicity of the anti-CD3 Fab-folate conjugate by two independent cytotoxicity assays. Dose-dependent T cell-mediated cytotoxicity with KB cells (FR+) but not A549 cells (FR−) treated with anti-CD3 Fab-folate in the presence of non-activated human PBMCs (ratio 1:10 of target: effector cells). Increasing concentrations of anti-CD3 Fab-folate were incubated with target cells for 12-24 h at 37° C. and 5% CO2.
Figure 5:
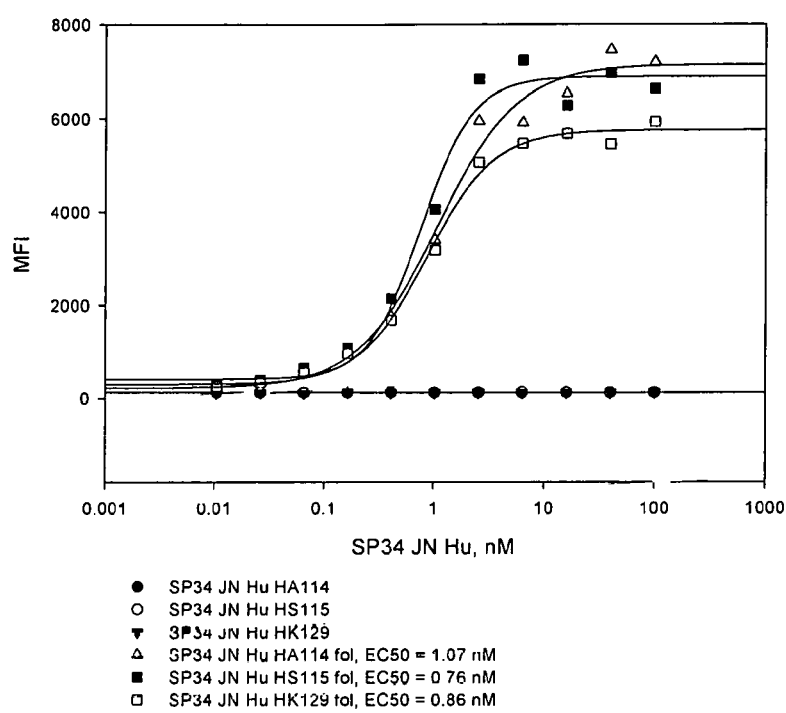
FIG. 5—Shows the binding of novel sequences SEQ ID NO: 1-15 of humanized SP34 Fabs and conjugates to SKOV-3 in an assay with folate-free medium, FIG. 6—Shows the binding of novel sequences SEQ ID NO: 1-15 of humanized SP34 Fabs and conjugates to SKOV-3 in an assay with 50 nM SFA medium.

We next tested the activity of the anti-CD3 Fab-folate conjugate in an in vitro cytotoxicity assay with KB and OV-90 cells ($FR^+$) and CAKI-1 and A549 cells ($FR^-$) as controls. Cells were co-cultured with activated human peripheral blood mononuclear cells (PBMCs; ratio 1:10 of target: effector cells) and treated with various concentrations of anti-CD3 Fab-folate or anti-CD3 Fab alone. Cytotoxicity was quantitated by measuring released LDH levels from lysed cells, and with CellTiter-Glo and FACS based toxicity assays. The anti-CD3 Fab-folate conjugate demonstrated efficient killing of KB and OV-90 cells in the presence of PBMCs with $EC_{50}$'s 10 pM and 100 pM respectively (FIG. 2A, Supplemental FIG. 4), while CAKI-1 cells (FIG. 2A) and A549 cells (Supplemental FIG. 4) were unaffected at 100 nM of conjugate. Treatment with anti-CD3 Fab alone induced negligible toxicity on all cell lines tested (FIG. 2A). Furthermore, incubation (16 hrs) of SKOV-3 cells (FIG. 2B) or KB cells (Supplemental FIG. 5) with activated PBMCs (ratio 1:10 of target: effector cells) in folate deficient media in the presence of the anti-CD3 Fab-folate conjugate resulted in the formation of rosettes, providing additional evidence for T cell targeting. In contrast, the anti-CD3 Fab had no effect on T cell engagement and clusters were not observed in the absence of PBMCs or KB cells (Supplemental FIG. 5).

Example 14

Figure 3:
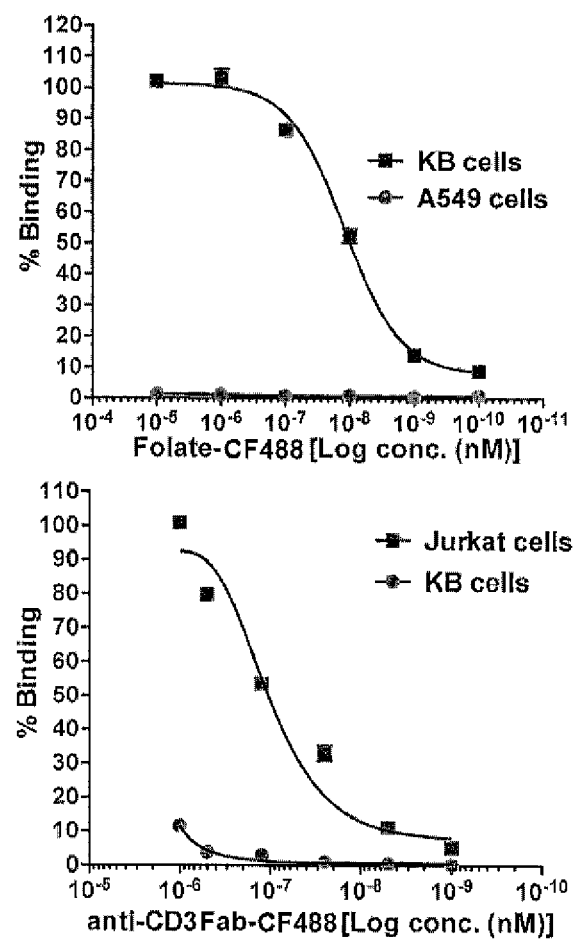
FIG. 3—Shows the binding of folate conjugates to FR and CD3.

We next examined the pharmacokinetics of the anti-CD3 Fab-folate conjugate and the unconjugated anti-CD3 Fab in rodents. A single dose of 1 mg/kg or 5 mg/kg of anti-CD3 Fab-folate in PBS or 1 mg/kg unconjugated anti-CD3 Fab was injected intravenously in three rats, and serum collected at regular intervals was analyzed by ELISA. The serum concentration decreased for both anti-CD3 Fab-folate and the corresponding unconjugated mutant anti-CD3 Fab at the same rate with a serum half-life of 60 mins (FIG. 3D). Thus, the anti-CD3 Fab-folate has similar pharmacokinetics to the unconjugated anti-CD3 Fab indicating that PK profile of the conjugate was not affected by folate derivatization.

Example 15

Figure 6:
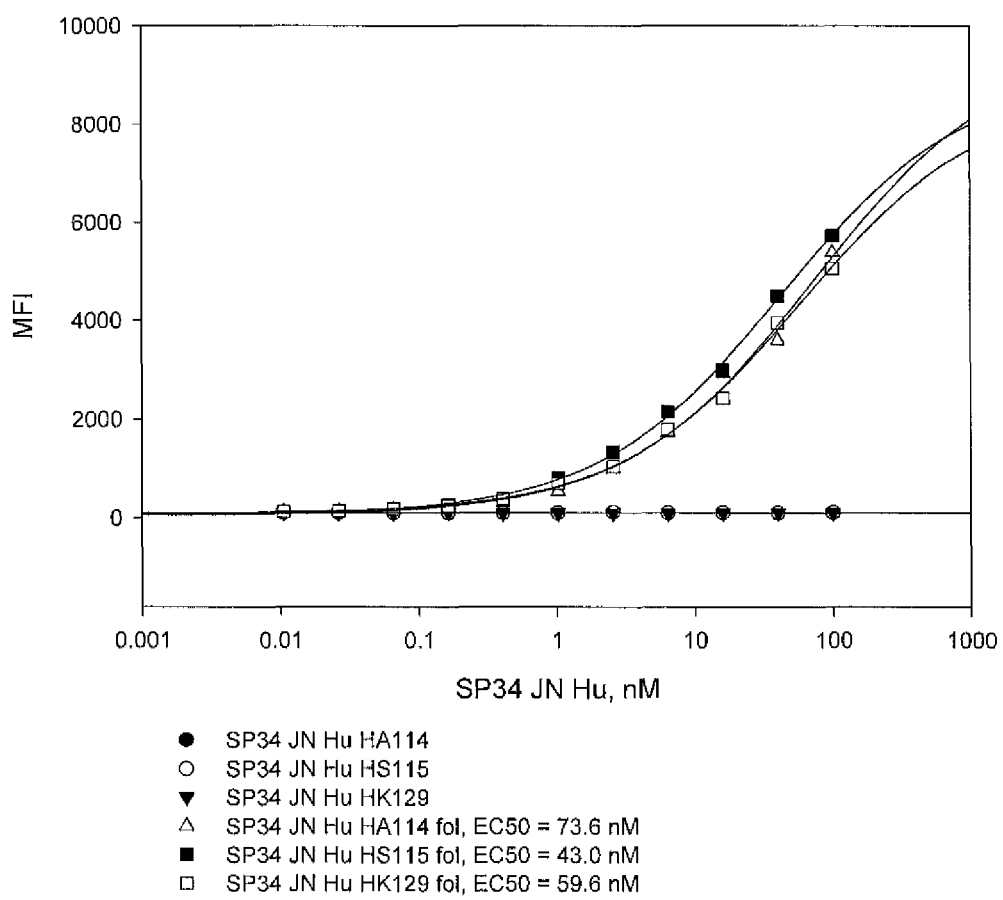
Figure 7:
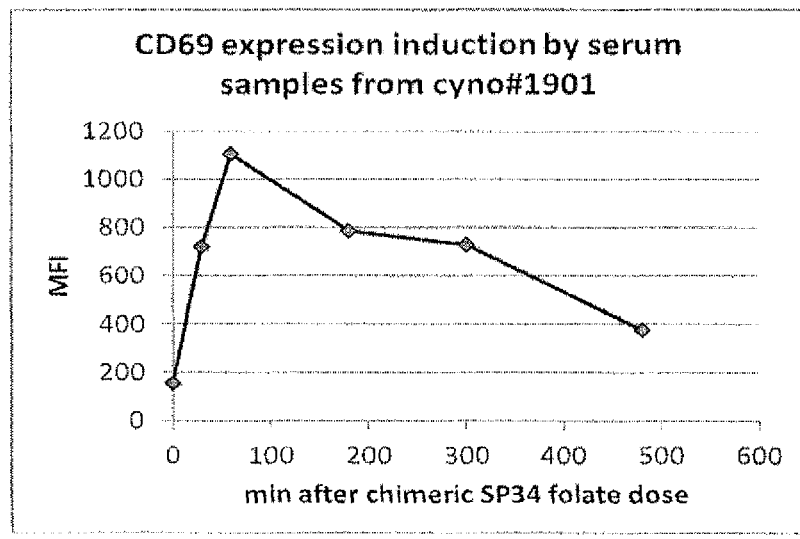
FIG. 7(a)—Shows CD69 expression induced by chimeric SP34 folate dosing.
FIG. 7(b)—Shows cell viability of HPB-ALL cells treated with the same serum samples from FIG. 7(a).
Figure 7:
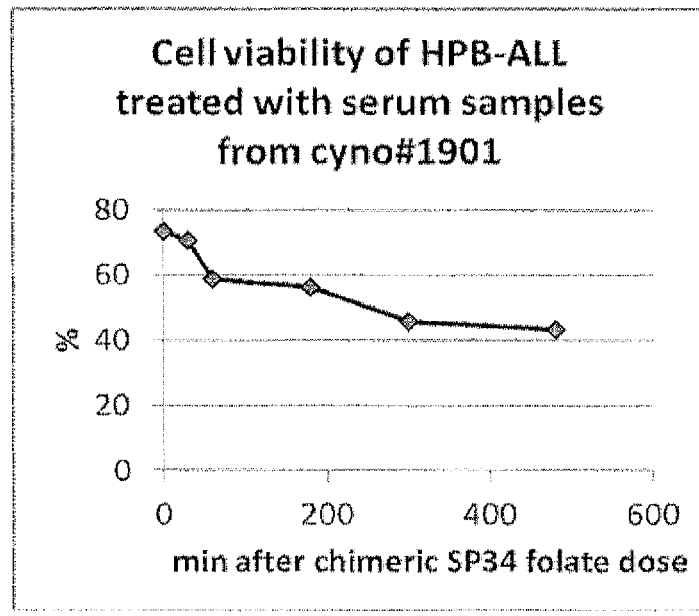
Figure 8:
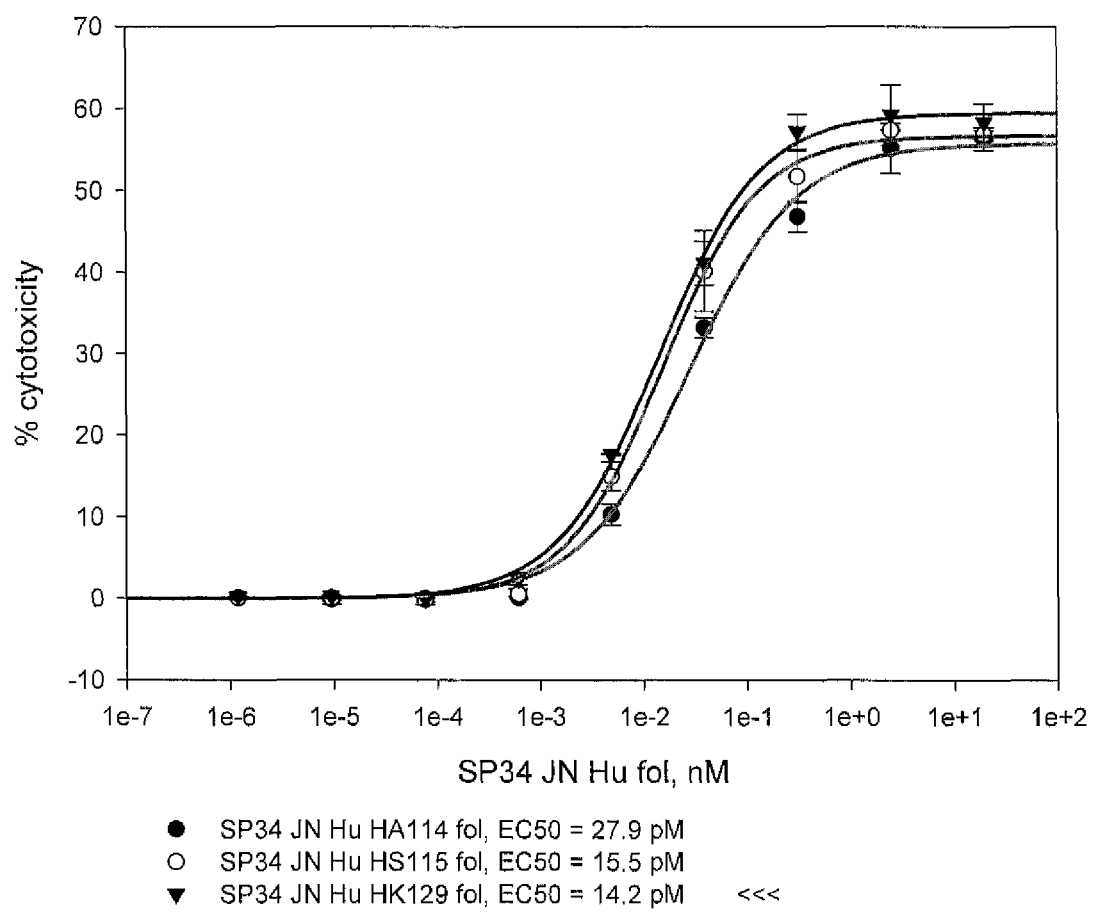
FIG. 8—is a killing assay showing percent cytotoxicity in human PBMC, repeating the 50 nM SPA conditions from FIG. 6.

The in vivo efficacy of the anti-CD3 Fab-folate bispecific agent was then assessed in a xenograft model using female NOD-SCID mice. Animals were maintained on a low-folate diet to reduce circulating serum levels of folate that might compete with the bispecific agent. KB ($FR^+$) or A549 ($FR^-$) cells were able to form tumors when mixed with non-activated human PBMCs (ratio 1:100 of target: effector cells) or activated human PBMCs (ratio 1:10 of target: effector cells) and injected subcutaneously into mice. We therefore implanted KB cells mixed with activated human PBMCs (ratio 1:10 of target: effector cells) into mice and injected the mice intravenously with 1.5 mg/kg of anti-CD3 Fab-folate or PBS daily for 10 days starting on the same day as tumor cell implantation. This dosing regimen was chosen based on the pharmokinetic properties of the anti-CD3 Fab-folate conjugate and previous studies with bispecific antibodies[10]. Tumor volumes showed a rapid increase in PBS treated mice with a doubling time of approximately 5 days. In contrast, tumors in mice treated with anti-CD3 Fab-folate were barely detectable throughout the duration of the study (FIG. 3A). In a parallel study, mice were implanted with KB cells mixed with unactivated human PBMCs (ratio 1:100 of target: effector cells) and treated intravenously with 1.5 mg/kg of anti-CD3 Fab-folate or PBS daily for 10 days starting on the same day as tumor cell implantation. Tumor volumes for both groups of mice decreased for the first 30 days of the study possibly due to the high burden of PBMCs at the injection site. The rate of decease of the tumors was, however, higher in anti-CD3 Fab-folate treated mice. After day 35 of the study, the tumors in PBS treated mice steadily increased in volume while tumors in the anti-CD3 Fab-folate treated mice decreased to barely detectable levels indicating the engagement of cytotoxic T cells for the elimination of the tumors by the anti-CD3 Fab-folate conjugate even in the absence of activated T cells. To test the in vivo selectivity of the anti-CD3 Fab-folate conjugate for FR expressing tumors, A549 cells ($FR^-$) were mixed with unactivated human PBMCs (ratio 1:100 of target: effector cells) and implanted in mice. Mice were treated in a similar manner with 10 daily intravenous doses of 1.5 mg/kg anti-CD3 Fab-folate and showed no significant difference from PBS treated tumors 20 days after treatment. Throughout all these studies no weight loss or other overt toxicity was observed in both anti-CD3 Fab-folate and PBS treated mice (FIG. 3C, Supplemental FIG. 6B). We further performed histopathological analysis of the mice both with and without anti-CD3 Fab-folate injection. Staining of kidneys from mice treated with anti-CD3 Fab-folate or PBS showed no infiltration of T cells; no obvious pathological differences in Hematoxylin and Eosin (H&E) staining between treatment and control groups were observed for other tissues such as spleen, lung and liver.

Example 16

Solid phase peptide synthesis (SPPS) was performed using a standard peptide synthesis apparatus. All peptides and peptide conjugates were purified using a preparative reverse phase-high performance liquid chromatography (RP-HPLC) instrument (Waters, xTerra C18 10 µm; 19×250 mm) and analyzed by analytical RP-HPLC (Waters, X-Bridge C18 5 µm; 3.0×50 mm) and Liquid chromatography/mass spectrometry (LC/MS). 1H spectra were acquired using a Varian 400 MHz NMR spectrometer. Samples were run in DMSO-d6/D2O; all 1H signals are recorded in ppm with reference to residual or DMSO (2.50 ppm), and data reported as s=singlet, d=doublet, t=triplet, q=quartet, and m=multiplet or unresolved, b broad, with coupling constants in Hz. Protein masses were obtained at Ambrx mass spectrometry facilities (La Jolla, CA).

Example 17

Construction of the Expression Plasmid, E. coli Cell Line W3110B60, Protein Production The expression plasmid (AXID) was constructed from pET-20b (+) and pET-24 (+) plasmids (EMD4Biosciences). The amber suppression cassette consisting of the modified M. jannaschii tRNA synthetase (specific for pAcPhe) was cloned into the BamHI site (type II cloning) of AXID. The UCHT1 Version2 Fab CD3 sequence was obtained from the literature[1,2] and sub-cloned into AXID vector downstream of the phoA promoter within the open reading frame. Lysine 136 of the heavy chain (HC-Lys136) was quickchanged (Stratagene) to the TAG amber nonsense codon. Wild-type E. coli K-12 W3110 cell line (ATCC) was engineered by homologous recombination[3] to have the following genotype: F-IN (rrnD-rrnE) lambda-araB::g1 tetA fhuA::dhfr proSW375R::cat. The temperature sensitive phenotype of proS in the W3110B60 genome was complemented by the wild-type, functional copy of the proS in this expression plasmid. The vector was transformed into W311B60 cells and cells were grown in defined media (2.1 L) supplemented with kanamycin sulfate (50 ug/mL) at 37° C., pH 7, and 480-1200 rpm (cascade) in a fermentor. At OD600=30, the pH was shifted to 6.8 for the production phase and defined media was added. pAcPhe dissolved in water (100 g/L) was then added to the fermentor. The dissolved oxygen was set point to maintain 30% with the primary agitation (480-1200 rpm). After 24 h, cells were harvested and UCHT1 was extracted from cells by osmotic shock by incubating with TES buffer [0.2 M Tris pH 8.0, 0.5 mM EDTA, 0.5 M sucrose) at a ratio of 4:1 (v/w) at 4° C. Extract was clarified by centrifugation (18000rpm, 20 min, and 4° C.), filtered through a 0.22micron filter, and loaded onto a Protein G column (GE healthcare). The column was washed with 5 bed volumes of PBS at pH 7.4, and protein was eluted with 10 bed volumes of 0.1 M glycine-HCl, pH 3.0. Fractions were collected into tubes containing 10% of 1 M Tris-HCl, pH 8. Pooled fractions were further purified by cation exchange [column: SP650S (Tosoh Bioscience), buffer A: 0.02 M phosphate (pH 6.0), buffer B: 0.02 M phosphate (pH 6.0) with 0.5M NaCl] and analyzed by SDS-PAGE gel and mass spectrometry.

Example 18

Synthesis of Folate-$N^{10}$(TFA)-Lys Linker (I)

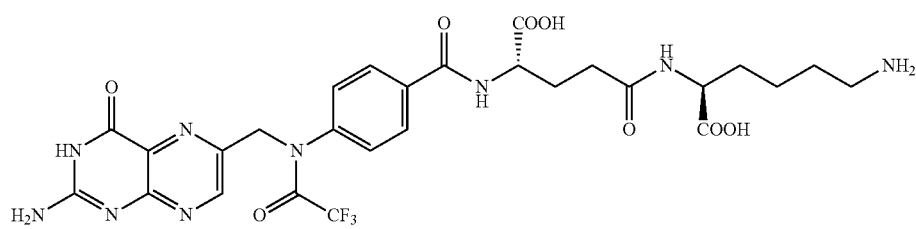

Folate-Lys was synthesized using standard solid phase peptide synthesis starting from H-Lys-(Boc)-2-ClTrt-Resin resin (Peptide international).[4] Briefly, H-Lys-(Boc)-2-C1Trt-Resin resin (500 mg, 0.89 mM) was swollen with DCM (5 mL) followed by (dimethyl formamide) (DMF, 5 mL). A solution of Fmoe-L-Glu(OtBu)-OH (1.5 equiv), HATU (1.5 equiv), and DIPEA (4.0 equiv) in DMF (3 mL) was added. Argon was bubbled for 2 h, and resin was washed with DMF (3×3 mL) and i-PrOH (3×3 mL), The coupling efficiency was assessed by the Kaiser Test. After swelling the resin in DMF (3 mL), a solution of pteroic acid (1.5 equiv), HATU (1.5 equiv), and DIPEA (4.0 equiv) in DMF (3 mL) was added. Argon was bubbled for 2 h, and resin was washed with DMF (3×3 mL) and i-PrOH (3×3 mL), The coupling efficiency was assessed by the Kaiser Test. After swelling the resin in DCM (3 mL) followed by drying under argon, final compound was cleaved from the resin using a trifluoroacetic acid (TFA):H2O;triisopropylsilane (95.5:2.5:2.5) cocktail (3×5 mL) directly to round bottom flask containing diethyl ether (300 mL) to obtain precipitated crude product. After filtering and drying, the crude product was purified using preparative reversed phase (RP)-HPLC (C18 column, 0% B-50% B in 25 min, buffer A: 0.1 TFA in water, buffer B: 0.1 TFA in acetonitrile, $\lambda$=280 nm), ACN was removed under vacuum, and pure fractions were freeze-dried to yield 1. as pale yellow solid. $^1$H NMR (DMSO-$d_6$/D$_2$O): $\delta$ 1.18 (m, 2H, Pep-H); 1.45 (m, 1H, Pep-H); 1.54 (m, 3H, Pep-H); 1.81 (m, 1H, Pep-H); 1.95 (m, 1H, Pep-H); 2.11 (m, 2H, Pep-H); 2.88 (m, 2H, Pep-H); 3.94 (m, 114, Lys-$\alpha$H); 4.12 (m, 1H, Glu-$\alpha$H); 4.46 (s, 2H, Pte-H); 6.61 (d, J=8.5 Hz, 2H, Pte-Ar—H); 7.56 (d, J=8.5 Hz, 2H, Pte-Ar—H); 8.60 (s, 1H, Pte-Ar—H). LC-MS (M+H)+: calcd for C27H30F3N9O8=665.6; found=666.0 g/mol.

Example 19

Synthesis of Phthalimide-PEG4-COOH

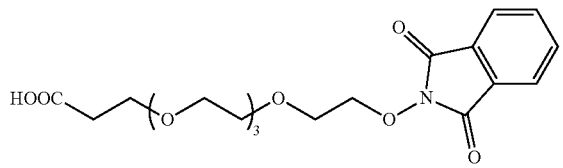

To a solution of triphenylphosphine (TPP, 216.7 mg, 0.826 mmol) and diethyl azodicarboxylate (DEAD, 143.9 mg, 0.826 mmol) in anhydrous THF (0.50 mL) at 0° C. under argon, $^t$BuOOC-PEG$_4$-OH (200.0 mg, 0.751 mmol), in anhydrous THF was added. After stirring the reaction for 15 min, a solution of N-hydroxy phthalimide (134.8 mg, 0.826 mmol) in anhydrous THF was added over 10 min. The reaction mixture was stirred at room temperature for 12 h under argon. After removing solvents under vacuum, TFA:triisopropylsilane:water (95:2.5:2.5; 5 mL) was added to the crude product and stiffed at room temperature for 1 h to deprotect tert-butyl group. The final product was purified by flash chromatography (hexane:EtOAc=1:1). Solvent of the combined pure fractions was evaporated under vacuum to yield final product as oily liquid. 1HNMR (CDCl3); δ 2.63 (m, 2H); 3,59-3.65 (m, 14H); 3.88 (m, 2H); 4.38 (m, 2H); 7.75 (m, 2H), 7.84 (m, 2H) LC/MS (ESI) (mlz): (M+H)$^+$ calcd. for C19H25NO9, 411.4, found, 411.4 g/mol.

Example 20

Synthesis of Phthalitnide-PEG4-NHS (2)

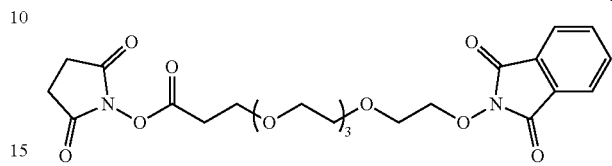

To a solution of HOOC-PEG4-O—N-phthalimide (50 mg, 0.122 mmol), N-hydroxysuccinimide (NHS, 15.4 mg, 0.134 mmol), and 4-dimethylaminopyridine (DMAP, 1.5 mg, 0.0122 mmol) in anhydrous DCM (0.5 mL) under argon, ethyl(dimethylaminopropyl) carbodiimide (EDC, 20.8 mg, 0.134 mmol) in anhydrous DCM (0.5 mL) followed was added. The reaction mixture was stirred at room temperature for 4 h under argon and purified using flash chromatography (hexane:DCM=1:1) to yield NHS-PEG4-O-N-phthalimide. Solvent of the combined pure fractions was removed under vacuum to yield final product as oily liquid. 1HNMR: δ 2.90 (t, J=6.4, 2H); 2.75 (bs, 4H); 3.56-3.63 (m, 12H), 3.833.87 (m, 4H), 4.37 (t, J=4.5, 2H); 7.75 (m, 2H), 7.83 (m, 2H),LC/MS (ESI) (m/z): (M+H)$^+$ calcd. for C23H28N2O11, 508.5, found, 509.0 g/mol.

Example 21

Synthesis of Folate-Lys-PEG4-phthatimide (3)

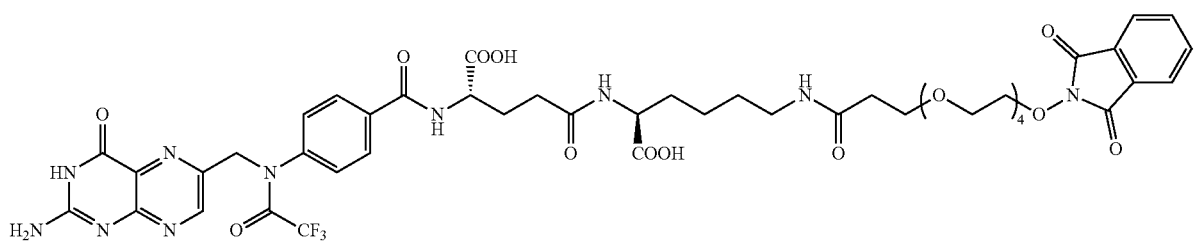

To a solution of NHS—OC-PEG4-O—N-phthalimide (21 mg, 0,041 mmol) and folate-N$^{10}$(TFA)-Lys (25 mg, 0.037 mmol) in anhydrous DMSO (300 µL) under argon, DIPEA (101.4 µL, 0.601 mmol) was added. The reaction mixture was continued to stir at room temperature for 2 h and progression of the reaction was followed by LC/MS. The final product was purified using RP preparative HPLC (C18 column, 0% B-50% B in 25 min, buffer A: 0.1 TFA in water, buffer B: 0.1 TFA in acetonitrile, λ=280 nm). After removing ACN under vacuum, pure fractions were freeze-dried to yield pale yellow solid. LC/MS (ESI) (m/z): (M+H)$^+$ calcd. for C46H53F3N10O16, 1058.9, found, 1059.0 g/mol.

Example 22

Synthesis of Folate-Lys-PEG4-aminooxy Linker (4)

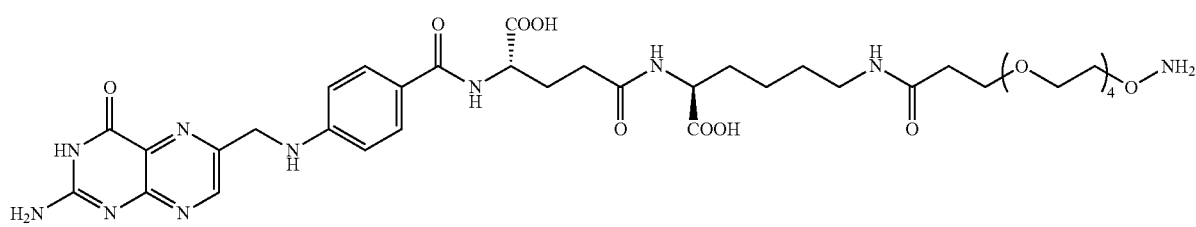

4

To a solution of folate-N10(TFA)-Lys-PEG-phthalimide (30 mg, 0.028 mmol) in DMSO (1 mL), hydrazine (13 µL, 0.42 mmol) was added and pH of the reaction was maintained at 9.35. Deprotection of phthalimide and TFA groups was monitored using LC/MS. Folate-Lys-PEG4-aminooxy linker was purified using reverse-phase preparative HPLC (C18 column, 0% B-50% B in 25 min, buffer A: 0.1 TFA in water, buffer B: 0.1 TFA in acetonitrile, $\lambda$=280 nm). After removing ACN under vacuum, pure fractions were freeze-dried to furnish yellow solid. $^1$H NMR (DMSO-$d_6$/$D_2O$) δ 1.88 (m, 1H, Pep-H); 2.03 (m, 1H, Pep-H); 2.15 (t, J=7.4, 2H); 2.28 (t, J=6.4, 2H); 3.05 (m, 4H); 3.20-3.60 (m, xH); 3.94 (m, 1H, Lys-αH); 4.23 (m, 1H, Glu-αH); 4.48 (s, 2H, Ptc-H); 6.64 (d, J=8.8 Hz, 2H, Ptc-Ar—H); 7.64 (d, J=8.8 Hz, 2H, Ptc-Ar—H); 8.63 (s, 1H, Pte-Ar—H); LC/MS (ESI) (m/z): (M+H)$^+$ calcd, for C36H52N10O13, 832.9 g/mol, found, 833.0 g/mol.

Example 23

Folate-anti-CD3 conjugation

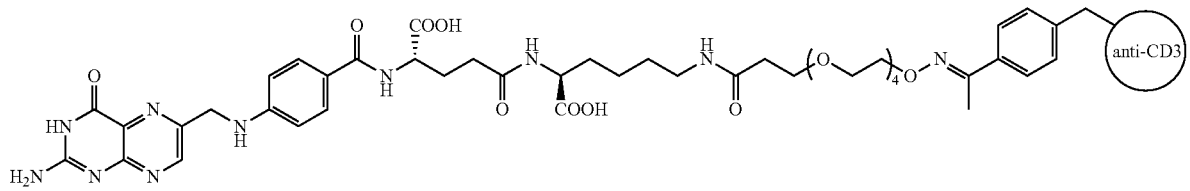

5

A solution of anti-CD3 Fab containing pAcPhe (10 mg, 0.21 µmol) in PBS pH 7.4 (1 mL) was buffer exchanged into 50 mM sodium acetate pH 4.0 (900 µL). After adding 1M acetic hydrazide (100 µL), folate-Lys-PEG4-aminooxy linker (1.7 mg, 2.10 µmol) was added to the reaction mixture and incubated at 28° C. for 48 hrs with shaking (50 rpm). Progress of the reaction was monitored by RP-HPLC (Zorbax 300SB CJ column, 4.6×150 mm; Agilent). Conjugates were eluted with a linear gradient from 30% B to 90% B (A, water, 0.1% TFA; B, Acetonitrile, 0.1% TFA). An Agilent 1100 series HPLC system and Chemstation software were used to resolve and quantify percentage of Fab conjugated with folate-linker. The reaction was completed within 48 h with >95% conversion efficiency. The final conjugate was purified using cation exchange column (SP650S, Tosoh Biosciences), buffer exchanged into PBS, and stored at 4° C. until use. Expected MS: 48539.64 Da, Observed MS: 48538.89 Da.

Example 24

In Vitro Efficacy Studies

Target cells-KB, OVCAR-3, SKOV-3, and OV-90 cells, were maintained in folate-free RPMI-1640 supplemented with 10% FBS and 100 units/ml of penicillin and 100 µg/ml of streptomycin for at least five passages before they were used for the assays. Jurkat and A549 cells were maintained in RPMI-1640 supplemented with 10% FBS and 100 units/ml of penicillin and 100 µg/ml of streptomycin. All the cells were grown as monolayers in a 5% carbon dioxide, 95% air-humidified atmosphere at 37° C.

For FR expression, cells were incubated with anti-FR-PE antibody (blue) and IgG1-Isotype-PE control (red) from R&D systems at 4° C. for 1 hrs and binding was assayed by flow cytometry. KB or A549 cells were seeded into a T75 flask and allowed to form a monolayer over 48 h. After trypsin digestion, cells were transferred into centrifuge tubes (1×10$^6$ cells/tube) and centrifuged. The medium was replaced with fresh medium containing increasing concentration of folate-FITC and incubated for 30 min at 4° C. After rinsing with fresh medium (2×1.0 mL) and PBS (1×1.0 mL), cells were resuspended in PBS (1.0 mL) and cell bound fluorescence was analyzed (30,000 cells/sample) using a flow cytometer. KB cells were plated into a T75 flask and allowed to form a monolayer over 48 h. After trypsin digestion, release cells were transferred into centrifuge tubes (1×10$^6$ cells/tube) and centrifuged. Spent medium in each tube was replaced with 100 nM FA-FITC in the presence of increasing concentration (0.1 nM 0.8 nM) of anti-CD3 Fab-folate in fresh medium (0.5 mL). After incubating for 30 min at 4° C., cells were rinsed with culture medium (2×1.0 mL) and PBS (1×1.0 mL) to remove any unbound radioactivity. Cells were then re-suspended in PBS (0.5 mL) and cell bound fluorescence was counted using a flow cytometer.

Human peripheral blood mononuclear cells (PBMC) were isolated from buffy coat (San Diego Blood Bank) using Ficoll Hypaque Plus (GE Heathcare) gradient centrifugation. In the event there were not enough cells from a single donor, several donors were used, but each were be kept separate (i.e., not mixed together) when used either in vitro or in vivo. PBMCs were activated with aCD3/aCD28 supramagnetic beads (Life Technologies) in the presence of rhIL-2 (100 ng/ml) and GMCSF (100 ng/ml).

For cytotoxicity assays, target cells were detached from the flasks with Accutase and seeded into U bottom 96-well plates. Activated PBMCs (effector cells) or non-activated PBMCs (effector cells) were added to the targeted cells at specified target: effector cells ratios. Anti-CD3 folate was diluted in complete culture medium added to the co-culture and after a brief centrifugation the plates were incubatated at 5% CO2 and at 37° C. for 24 hrs. For cytotoxicity by LDH release, LDH was measured using a kit from Promega as per manufacturer's instructions. For cytotoxicity by flow cytometry, cells were labeled with DIO (green plasma membrane stain) and propidium iodide was added to a final concentration of 1 μg/mL.[9] For cytotoxicity by ATP content, PBMCs were washed off after 24 hrs and ATP content of KB cells was measured using Cell Titer Glo (Promega).

Example 25

Pharmacokinetic Study

Anti-CD3 Fab-folate and unconjugated CD3 Fab were administered to Sprague-Dawley rats (Charles River Laboratories) as a single bolus intravenous injection. Blood was collected at regular intervals and anti-CD3 Fab-folate was quantified in rat serum by ELISA. The pharmacokinetic properties of the conjugates were measured as time vs. serum concentration.

Example 26

In Vivo Efficacy Studies 6- to 8-wk-old female NOD-SCID mice were purchased from either from TSRI animal facilities or from The Jackson Laboratory and maintained on gamma-irradiated folate-deficient special diet (Teklad) for at least 2 weeks before the start of the study. Animals were housed 5/cage in a barrier, pathogen-free cloaked rack. Autoclaved tap water and food were given ad libitum. Mice were identified individually by tattoo at the base of the tail or ear punch. All animal procedures were approved by The Scripps Research Institute Animal Care and Use Committee and Ambrx, Inc. Animal Care and Use Committee and were performed according to national and international guidelines for the humane treatment of animals.

Tumor cells (KB cells at $5 \times 10^5$/mouse) were mixed with activated or non-activated PBMCs (in the specified target: effector cells ratios) and implanted sub-cutaneous in the left flank as 200 ul injections. Animals were treated IV with 1.5 mg/kg anti-CD3 Fab-folate or PBS daily for 10 injections (black arrows) starting on the same day as tumor cell implantation, with an occasional 2-day break in dosing to accommodate for weekends. Tumor growth was monitored biweekly by measuring in two perpendicular directions and the volumes were estimated using the formula $V=(L \times W \times W)/2$ where V=volume, W=shortest diameter, and L=longest diameter. Body weight was determined by weighing the mice on an electronic weighing machine. The experiments were terminated when group average tumor size reached approximately 1,000 mm3 or 35 days after start of dosing, whichever occurs first.

For immunohistochemical analysis, animals were sacrificed using Isoflurane and tumors as well as various organs were isolated and fixed in Formalin-Zinc overnight. Tissues were embedded in paraffin and sectioned for staining. Hematoxylin and Eosin (H&E) staining was performed as per standard protocols and slides were scanned using a Leica Scanner.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference herein in their entirety for all purposes.

What is claimed is:

1. An anti-human CD3 antibody, comprising (a) a heavy chain amino acid sequence comprising a sequence selected from the group consisting of SEQ ID NOs: 1, 2 and 3, (b) a light chain amino acid sequence comprising a sequence selected from the group consisting of SEQ ID NOs: 4, 5 and 6, and (c) a non-naturally encoded amino acid substituted for position 114Ala of the heavy chain, position 115Ser of the heavy chain, or position 129Lys of the heavy chain, wherein said non-naturally encoded amino acid is para-acetyl-phenylalanine, para-azido-phenylalanine or p-propargyloxyphenylalanine.

2. The anti-human CD3 antibody of claim 1, comprising (a) the heavy chain amino acid sequence comprising the amino acid sequence of SEQ ID NO: 3, and (b) the light chain amino acid sequence comprising the amino acid sequence of SEQ ID NO: 6.

3. The anti-human CD3 antibody of claim 1, wherein the anti-human CD3 antibody comprises one or more post-translational modifications.

4. The anti-human CD3 antibody of claim 1, wherein the anti-human CD3 antibody is linked to a linker, a polymer, or a biologically active molecule.

5. The anti-human CD3 antibody of claim 4, wherein the biologically active molecule is folate.

6. The anti-human CD3 antibody of claim 5, wherein the the folate is attached to the non-naturally encoded amino acid.

7. The anti-human CD3 antibody of claim 1, wherein the non-naturally encoded amino acid is para-acetyl-phenylalanine.

8. The anti-human CD3 antibody of claim 1, wherein the non-naturally encoded amino acid is linked to a water soluble polymer.

9. The anti-human CD3 antibody of claim 8, wherein the water soluble polymer comprises a poly(ethylene glycol) moiety.

10. A bispecific binding molecule, comprising i) a first binding domain that is folate and that specifically binds to a folate receptor, and ii) a second binding domain, the second binding domain comprising (a) a heavy chain amino acid sequence comprising a sequence selected from the group consisting of SEQ ID NOs: 1, 2, and 3, (b) a light chain amino acid sequence comprising a sequence selected from the group consisting of SEQ ID NOs: 4, 5 and 6, and (c) a non-naturally encoded amino acid substituted for position 114Ala of the heavy chain, position 115Ser of the heavy chain, or position 129Lys of the heavy chain, wherein said non-naturally encoded amino acid is para-acetyl-phenylalanine, para-azido-phenylalanine or p-propargyloxyphenylalanine.

11. The bispecific binding molecule of claim 10, wherein the second binding domain comprises one or more post-translational modifications.

12. The bispecific binding molecule of claim 10, wherein the second binding domain is linked to a linker, a polymer, or a biologically active molecule.

13. The bispecific binding molecule of claim 12, wherein the biologically active molecule is folate.

14. The anti-human CD3 antibody of claim 13, wherein the folate is attached to the non-naturally encoded amino acid.

15. An anti-human CD3 antibody, wherein the anti-human CD3 antibody comprises a binding domain comprising (a) a variable heavy chain domain comprising an amino acid sequence selected from the group consisting of SEQ ID NOs: 1, 2 and 3, (b) a variable light chain domain comprising an-amino acid sequence selected from the group consisting of SEQ ID NOs: 4, 5 and 6, and (c) a non-naturally encoded amino acid substituted for position 114Ala of the variable heavy chain domain, position 115Ser of the variable heavy chain domain, or position 129Lys of the variable heavy chain domain, wherein said non-naturally encoded amino acid is para-acetyl-phenylalanine, para-azido-phenylalanine or p-propargyloxyphenylalanine.

16. The anti-human CD3 antibody of claim 15, wherein the anti-human CD3 antibody is linked to a linker, a polymer, or a biologically active molecule.

17. The anti-human CD3 antibody of claim 16, wherein the biologically active molecule is folate.

18. The anti-human CD3 antibody of claim 17, wherein the folate is attached to the non-naturally encoded amino acid.

19. The anti-human CD3 antibody of claim 15, wherein the non-naturally encoded amino acid is para-acetyl-phenylalanine.

20. A pharmaceutical composition, comprising a therapeutically effective amount of the anti-human CD3 antibody of claim 1, and a pharmaceutically acceptable carrier or excipient.

21. A pharmaceutical composition, comprising a therapeutically effective amount of the bispecific binding molecule of claim 10, and a pharmaceutically acceptable carrier or excipient.

22. The anti-human CD3 antibody of claim 10, wherein the non-naturally encoded amino acid is para-acetyl-phenylalanine.

23. A pharmaceutical composition, comprising a therapeutically effective amount of the anti-human CD3 antibody of claim 15, and a pharmaceutically acceptable carrier or excipient.

* * * * *